US008080567B2

(12) United States Patent
Oxford et al.

(10) Patent No.: US 8,080,567 B2
(45) Date of Patent: *Dec. 20, 2011

(54) EP₂ RECEPTOR AGONISTS

(75) Inventors: Alexander William Oxford, Royston (GB); Richard Jon Davis, Royston (GB); Robert Alexander Coleman, Royston (GB); Kenneth Lyle Clark, Linton (GB); David Edward Clark, Harlow (GB); Shirley Ann Brunton, Abingdon (GB); Neil Victor Harris, Harlow (GB); Garry Fenton, Harlow (GB); George Hynd, Harlow (GB); Keith Alfred James Stuttle, Harlow (GB); Jonathan Mark Sutton, Harlow (GB); Mark Richard Ashton, Abingdon (GB); Edward Andrew Boyd, Abingdon (GB)

(73) Assignee: Asterand UK Limited, Royston, Hertfordshire (GB)

( * ) Notice: Subject to any disclaimer, the term of this patent is extended or adjusted under 35 U.S.C. 154(b) by 454 days.

This patent is subject to a terminal disclaimer.

(21) Appl. No.: 12/063,421

(22) PCT Filed: Aug. 9, 2006

(86) PCT No.: PCT/GB2006/002979
§ 371 (c)(1),
(2), (4) Date: Feb. 8, 2008

(87) PCT Pub. No.: WO2007/017687
PCT Pub. Date: Feb. 15, 2007

(65) Prior Publication Data
US 2010/0130556 A1    May 27, 2010

Related U.S. Application Data

(60) Provisional application No. 60/706,431, filed on Aug. 9, 2005.

(30) Foreign Application Priority Data

Aug. 10, 2005    (GB) .................................. 0516439.7

(51) Int. Cl.
*A61K 31/44* (2006.01)
*A61K 31/42* (2006.01)
*A61K 31/195* (2006.01)

(52) U.S. Cl. .......................... 514/336; 514/375; 514/563
(58) Field of Classification Search ........................ None
See application file for complete search history.

(56) References Cited

U.S. PATENT DOCUMENTS

| | | | |
|---|---|---|---|
| 5,576,347 A | 11/1996 | Sredni et al. | |
| 5,939,332 A | 8/1999 | Lee et al. | |
| 6,562,868 B1 | 5/2003 | Stjernschantz et al. | |
| 7,326,732 B2 | 2/2008 | Oxford et al. | |
| 7,662,839 B2 | 2/2010 | Oxford et al. | |
| 2005/0209336 A1 | 9/2005 | Borman et al. | |
| 2009/0298899 A1 | 12/2009 | Oxford et al. | |

FOREIGN PATENT DOCUMENTS

| | | |
|---|---|---|
| DE | 2293101 | 3/1996 |
| WO | 98/27976 A1 | 7/1998 |
| WO | 98/34916 A1 | 8/1998 |
| WO | 00/27823 A1 | 5/2000 |
| WO | 00/31084 A1 | 6/2000 |
| WO | 00/40248 | 7/2000 |
| WO | 01/46140 A1 | 6/2001 |
| WO | 01/85167 A1 | 11/2001 |
| WO | 02/24647 A1 | 3/2002 |
| WO | 03/032972 | 4/2003 |
| WO | 03/037433 A1 | 5/2003 |
| WO | 03/040126 A1 | 5/2003 |
| WO | 03/045371 A1 | 6/2003 |
| WO | 2004007439 | 1/2004 |
| WO | 2004/012656 A2 | 2/2004 |
| WO | 2005/037812 A1 | 4/2005 |
| WO | 2005/061449 A1 | 7/2005 |
| WO | 2005/080367 A1 | 9/2005 |

OTHER PUBLICATIONS

Han (Advances in Characterization of Pharmaceutical Hydrates. Trends in Bio/Pharmaceutical Industry, pp. 25-29. Mar. 2006).*
Vippagunta et al (Adv Drug Deliv Rev 48:3-26, 2001).*
Anderson (Chem and Biol 10:787-797, 2003).*
Thiel (Nature Biotechnol 2:513-519, 2004).*
Tani et al (Bioorg Med Chem 10:1093-1106, 2002).*
Berge, Stephen M., et al.; "Pharmaceutical Salts"; Journal of Pharmaceutical Sciences, vol. 66, No. 1; pp. 1-19 (Jan. 1977).
Griffiths, Christopher E.M., "T-Cell-Targeted Biologicals for Psoriasis"; Current Drugs Targets—Inflammation & Allergy; 3, pp. 157-161 (2004).
Lebwohl, Mark; "Psoriasis"; Seminar, The Lancet, vol. 361; pp. 1197-1204 (Apr. 5, 2003) (www.thelancet.com).
Nataraj, Chandra, et. al.; "Receptors for prostaglandin E2 that regulate cellular immune responses in the mouse"; J. Clin. Invest.; 108; pp. 1229-1235 (2001) (doi: 10.1172/JCI2001 113640).
Salim, Asad & Emerson, Russell; "Targeting interleukin-2 as a treatment for psoriasis"; Current Opinion in Investigational Drugs; vol. 2, No. 11, (2001); pp. 1546-1548.
Tilley, Stephen L., et. al.; "Receptors and pathways mediating the effects of prostaglandin E2 on airway tone"; American Journal of Physiology Lung Cellular and Molecular Physiology; AJP—Lung 284; pp. 599-606 (2003); (doi: 10.1152/ajplung.00324.2002).
Useato, Shinichi, et. al.; "Novel Histone Deacetylase Inhibitors: N-Hydroxycarboxamides Possessing a Terminal Bicyclic Aryl Group"; Bioorganic and Medicinal Chemistry Letters 12 (2002); pp. 1347-1349.
Coleman, Robert A., et al.; "Classification of Prostanoid Receptors: Properties, Distribution, and Structure of the Receptors and Their Subtypes"; International Union of Pharmacology, Pharmacological Reviews, vol. 46, No. 2, pp. 205-229; The American Society for Pharmacology and Experimental Therapeutics (1994).
Chemical Abstract Accession No. 2003:31915608; Otava Stock Chemicals Catalogue, Oct. 26, 2003, compound with CAS Registry No. 620545-88-3.
Chemical Abstract Accession No. 2003:3848742; Akos Sample Catalogue Feb. 9, 2004, compound with CAS Registry No. 618413-90-4.
Chemical Abstract Accession No. 2003:3849399; Akos Sample Catalogue, Feb. 9, 2004, compound with CAS Registry No. 618404-52-7.
Chemical Abstract Accession No. 2003:3849331; Akos Sample Catalogue, Feb. 9, 2004, compound with CAS Registry No. 618401-55-1.

Morissette, et al. Advanced Drug Delivery Reviews 2004, vol. 56, pp. 275-3000.

Patani, George A., Bioisosterism: A rational Approach in Drug Design. Chem. Rev. 96, 1996, pp. 3147-3176.

Youssefyeh, Raymond D., Development of a Novel Series of (2-Quinolinylmethoxy)phenyl-Containing Compounds as High-Affinity Leukotriene Receptor Antagonists. 1. Initial Structure-Activity Relationships. J. Med. Chem. 33 (1990) 1186-1194.

* cited by examiner

*Primary Examiner* — Brandon Fetterolf
*Assistant Examiner* — Craig Ricci
(74) *Attorney, Agent, or Firm* — Honigman Miller Schwartz & Cohn LLP; Cynthia M. Bott

(57) ABSTRACT

A compound of formula (III): or a salt, solvate and chemically protected form thereof, wherein: $R^5$ is an optionally substituted $C_{5-20}$ aryl or $C_{4-20}$alkyl group; L' is a single bond, —O— or —C(=O)—; A is selected from the group consisting of: formula (i) (ii) (iii) wherein X and Y are selected from the group consisting of: O and $CR^3$; S and $CR^3$; NH and $CR^3$; NH and N; O and N; S and N; N and S; and N and O, and where the dotted lines indicate a double bond in the appropriate location, and where Q is either N or CH; D is selected from: formula (i) (ii) (iii) (iv) (v) (vii) (viii) (ix) B is selected from the group consisting of: formula (A) (B) where $R^{P6}$ is selected from fluoro and chloro; and $R^2$ is either: (i) —$CO_2H$; (ii) —$CONH_2$; (iii) —$CH_2$—OH; or (iv) tetrazol-5-yl.

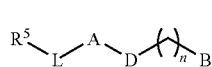

(III)

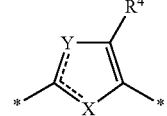

(i)

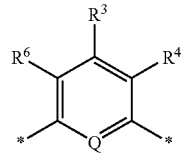

(ii)

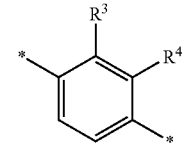

(iii)

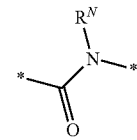

(i)

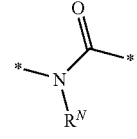

(ii)

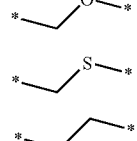

(iii)

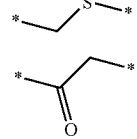

(iv)

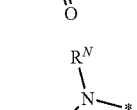

(v)

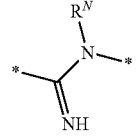

(vi)

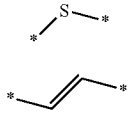

(vii)

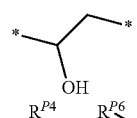

(viii)

(ix)

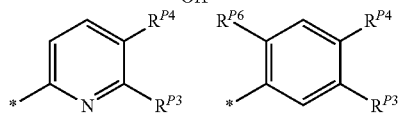

21 Claims, No Drawings

EP₂ RECEPTOR AGONISTS

This invention relates to EP₂ receptor agonists, pharmaceutical compositions comprising such compounds, and the use of such compounds and compositions to treat various diseases.

BACKGROUND TO THE INVENTION

Prostanoids comprise prostaglandins (PGs) and thromboxanes (Txs) and their receptors fall into five different classes (DP, EP, FP, IP and TP) based on their sensitivity to the five naturally occurring prostanoids, $PGD_2$, $PGE_2$, $PGF_{2\alpha}$, $PGI_2$ and $TxA_2$, respectively (Coleman, R. A., Prostanoid Receptors. *IUPHAR compendium of receptor characterisation and classification*, 2nd edition, 338-353, ISBN 0-9533510-3-3, 2000). EP receptors (for which the endogenous ligand is $PGE_2$) have been subdivided into four types termed $EP_1$, $EP_2$, $EP_3$ and $EP_4$. These four types of EP receptors have been cloned and are distinct at both a molecular and pharmacological level (Coleman, R. A., 2000)

$EP_2$ agonists have been shown to be effective in the treatment of a number of conditions, including (but not limited to) dysmenorrhoea (WO 03/037433), pre-term labour (GB 2 293 101), glaucoma (WO 03/040126), ocular hypertension (WO 03/040126), immune disorders (Nataraj, C., at al., *J. Clin. Invest.*, 108, 1229-1235 (2001)), osteoporosis (WO 98/27976, WO 01/46140), asthma (Tilley, et al., *Am. J. Physiol. Lung Cell Mol. Physiol.*, 284, L599-606 (2003)), allergy, bone disease (WO 02/24647), fracture repair (WO 98/27976, WO 02/24647), male sexual dysfunction (WO 00/40248), female sexual dysfunction (U.S. Pat. No. 6,562,868), periodontal disease (WO 00/31084), gastric ulcer (U.S. Pat. No. 5,576,347) and renal disease (WO 98/34916).

In co-pending applications GB 0329620.9, filed 22 Dec. 2003 and a corresponding US provisional application filed 24 Dec. 2003, which are hereby incorporated by reference, it has been shown that $EP_2$ agonists inhibit lymphocyte activation and the release of pro-inflammatory cytokines from alveolar macrophages. In addition, $EP_2$ activation inhibits monocyte and neutrophil activation. Thus, $EP_2$ agonists should prove useful in the treatment of inflammatory and immune disorders such as psoriasis, dermatitis, rheumatoid arthritis, multiple sclerosis, scleroderma, transplant rejection, allergy, systemic lupus erythematosus, vasculitis, type 1 diabetes mellitus, and inflammatory lung diseases such as chronic obstructive pulmonary disease, asthma, acute respiratory distress syndrome and cystic fibrosis.

In addition, $EP_2$ agonists can also be used in the treatment of fibrosis, including, but not limited to idiopathic pulmonary fibrosis, scleroderma and systemic sclerosis, post-operative fibrosis following trabulectomy, liver repair and regeneration following cirrhosis, hepatitis, toxicity, cancer or renal fibrosis. $EP_2$ agonists can also be used in the prevention of fibroblast to myofibroblast conversion to treat asthma and other fibrotic lung diseases. $EP_2$ agonists may also be used to maintain ductus arteriosus patency in infants with congenital heart disease.

Compounds which combine $EP_2$ receptor agonist and $EP_4$ receptor antagonist properties may prove useful in the treatment of several diseases including myometrial disorders, bone diseases including osteoporosis and osteoarthritis, allergic and immune disorders such as psoriasis, transplant rejection, and asthma, inflammatory diseases such as rheumatoid arthritis, chronic obstructive pulmonary disease and acute respiratory disease syndrome, and fibrotic lung diseases.

SUMMARY OF THE INVENTION

A first aspect of the present invention provides a compound of formula (I):

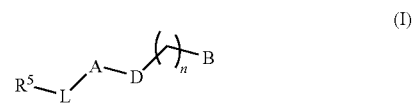

or a salt, solvate and chemically protected form thereof, wherein:

$R^5$ is an optionally substituted $C_{5-20}$ aryl or $C_{4-20}$ alkyl group;

L is —O— or —C(=O)—;

A is selected from the group consisting of:

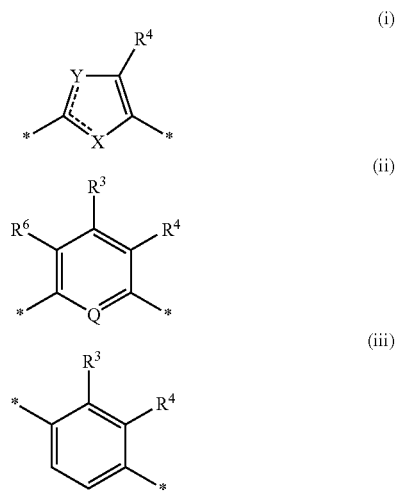

wherein X and Y are selected from the group consisting of: O and $CR^3$; S and $CR^3$; NH and $CR^3$; NH and N; O and N; S and N; N and S; and N and O, and where the dotted lines indicate a double bond in the appropriate location, and where Q is either N or CH;

$R^3$ is selected from H, F, Cl and optionally substituted $C_{1-4}$ alkyl, $C_{1-4}$ alkoxy, $C_{5-7}$ aryl and $C_{5-7}$ aryl-$C_{1-4}$ alkyl groups;

$R^4$ is selected from H, F, Cl and optionally substituted $C_{1-4}$ alkyl, $C_{1-4}$ alkoxy, $C_{5-7}$ aryl and $C_{5-7}$ aryl-$C_{1-4}$ alkyl groups;

$R^5$ is selected from H, F, Cl and optionally substituted $C_{1-4}$ alkyl, $C_{1-4}$ alkoxy, $C_{5-7}$ aryl and $C_{5-7}$ aryl-$C_{1-4}$ alkyl groups;

D is selected from:

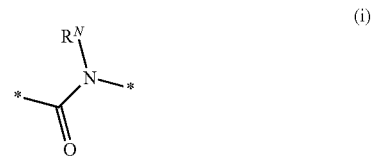

-continued

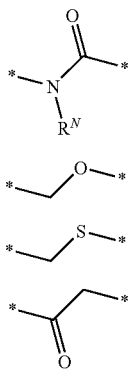

B is selected from the group consisting of:

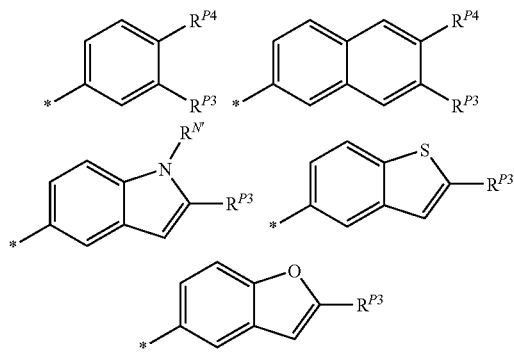

where $R^{N'}$ is selected from H and $C_{1-4}$ alkyl;
where one of $R^{P3}$ and $R^{P4}$ is —$C_m$ alkylene-$R^2$ and the other of $R^{P3}$ and $R^{P4}$ is H, m and n can be 0 or 1, and m+n=1 or 2; and additionally when $R^{P3}$ is —$C_m$ alkylene-$R^2$, m can also be 2 or 3, and m+n=1, 2, 3 or 4, and when $R^2$ is tetrazol-5-yl, m+n may be 0;
and where B is selected from the group consisting of:

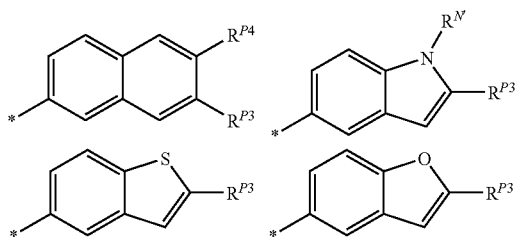

m+n can also equal 0;
or where one of $R^{P3}$ and $R^{P4}$ is —O—CH$_2$—$R^2$, and the other of $R^{P3}$ and $R^{P4}$ is H, n is 0;

$R^N$ is H or optionally substituted $C_{1-4}$ alkyl;
$R^2$ is either:
(i) —CO$_2$H (carboxy);
(ii) —CONH$_2$;
(iii) —CH$_2$—OH; or
(iv) tetrazol-5-yl.

A second aspect of the present invention provides a compound of formula (II):

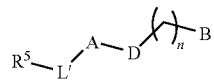

or a salt, solvate and chemically protected form thereof, wherein:
$R^5$ is an optionally substituted $C_{5-20}$ aryl or $C_{4-20}$ alkyl group;
L' is a single bond, —O— or —C(=O)—;
A is selected from the group consisting of:

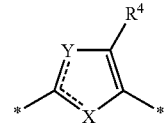

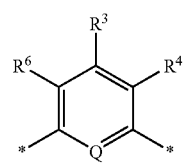

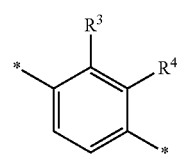

wherein X and Y are selected from the group consisting of: O and CR$^3$; S and CR$^3$; NH and CR$^3$; NH and N; O and N; S and N; N and S; and N and O, and where the dotted lines indicate a double bond in the appropriate location, and where Q is either N or CH;
$R^3$ is selected from H, F, Cl and optionally substituted $C_{1-4}$ alkyl, $C_{1-4}$ alkoxy, $C_{5-7}$ aryl and $C_{5-7}$ aryl-$C_{1-4}$ alkyl groups;
$R^4$ is selected from H, F, Cl and optionally substituted $C_{1-4}$ alkyl, $C_{1-4}$ alkoxy, $C_{5-7}$ aryl and $C_{5-7}$ aryl-$C_{1-4}$ alkyl groups;
$R^6$ is selected from H, F, Cl and optionally substituted $C_{1-4}$ alkyl, $C_{1-4}$ alkoxy, $C_{5-7}$ aryl and $C_{5-7}$ aryl-$C_{1-4}$ alkyl groups;
D is selected from:

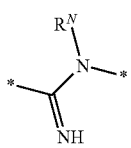

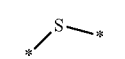

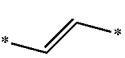

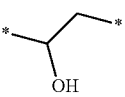

B is selected from the group consisting of:

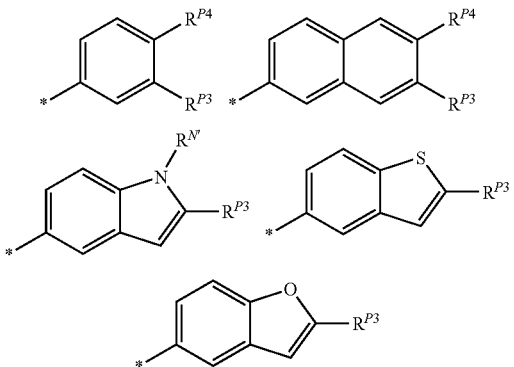

where $R^{N'}$ is selected from H and $C_{1-4}$ alkyl;
where one of $R^{P3}$ and $R^{P4}$ is —$C_m$ alkylene-$R^2$ and the other of $R^{P3}$ and $R^{P4}$ is H, m and n can be 0 or 1, and m+n=1 or 2; and additionally when $R^{P3}$ is —$C_m$ alkylene-$R^2$, m can also be 2 or 3, and m+n=1, 2, 3 or 4, and when $R^2$ is tetrazol-5-yl, m+n may be 0;
and where B is selected from the group consisting of:

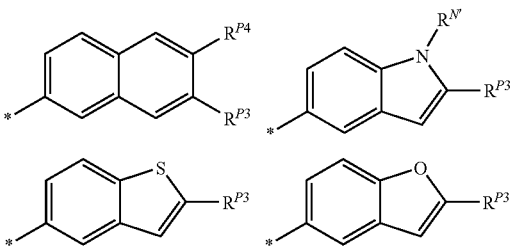

m+n can also equal 0;
or where one of $R^{P3}$ and $R^{P4}$ is —O—CH$_2$—$R^2$, and the other of $R^{P3}$ and $R^{P4}$ is H, n is 0;
$R^N$ is H or optionally substituted $C_{1-4}$ alkyl;
$R^2$ is either:
(i) —CO$_2$H (carboxy);
(ii) —CONH$_2$;
(iii) —CH$_2$—OH; or
(iv) tetrazol-5-yl.

A third aspect of the present invention provides a compound of formula (III):

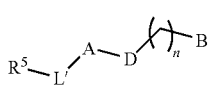

(III)

or a salt, solvate and chemically protected form thereof, wherein:
$R^5$ is an optionally substituted $C_{5-20}$ aryl or $C_{4-20}$ alkyl group;
$L'$ is a single bond, —O— or —C(=O)—;

A is selected from the group consisting of:

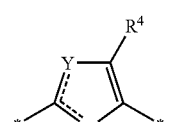
(i)

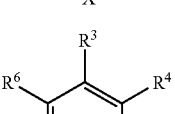
(ii)

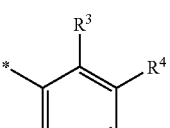
(iii)

wherein X and Y are selected from the group consisting of: O and CR$^3$; S and CR$^3$; NH and CR$^3$; NH and N; O and N; S and N; N and S; and N and O, and where the dotted lines indicate a double bond in the appropriate location, and where Q is either N or CH;
$R^3$ is selected from H, F, Cl and optionally substituted $C_{1-4}$ alkyl, $C_{1-4}$ alkoxy, $C_{5-7}$ aryl and $C_{5-7}$ aryl-$C_{1-4}$ alkyl groups;
$R^4$ is selected from H, F, Cl and optionally substituted $C_{1-4}$ alkyl, $C_{1-4}$ alkoxy, $C_{5-7}$ aryl and $C_{5-7}$ aryl-$C_{1-4}$ alkyl groups;
$R^6$ is selected from H, F, Cl and optionally substituted $C_{1-4}$ alkyl, $C_{1-4}$ alkoxy, $C_{5-7}$ aryl and $C_{5-7}$ aryl-$C_{1-4}$ alkyl groups;
D is selected from:

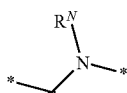
(i)

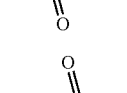
(ii)

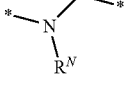
(iii)

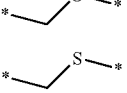
(iv)

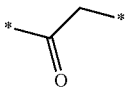
(v)

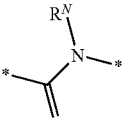
(vi)

-continued

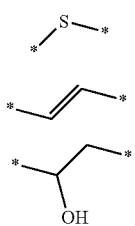

(vii)

(viii)

(ix)

B is selected from the group consisting of:

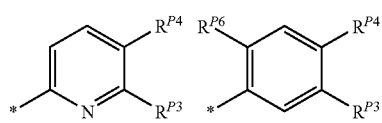

where $R^{P6}$ is selected from fluoro and chloro;
where one of $R^{P3}$ and $R^{P4}$ is —$C_m$ alkylene-$R^2$ and the other of $R^{P3}$ and $R^{P4}$ is H, m and n can be 0 or 1, and m+n=1 or 2; and additionally when $R^{P3}$ is —$C_m$ alkylene-$R^2$, m can also be 2 or 3, and m+n=1, 2, 3 or 4, and when $R^2$ is tetrazol-5-yl, m+n may be 0;
or where one of $R^{P3}$ and $R^{P4}$ is —O—$CH_2$—$R^2$, and the other of $R^{P3}$ and $R^{P4}$ is H, n is 0;
$R^N$ is H or optionally substituted $C_{1-4}$ alkyl;
$R^2$ is either:
(i) —$CO_2H$ (carboxy);
(ii) —$CONH_2$;
(iii) —$CH_2$—OH; or
(iv) tetrazol-5-yl.

A fourth aspect of the present invention provides a compound of formula (IV):

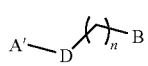

(IV)

or a salt, solvate and chemically protected form thereof, wherein:
A' is:

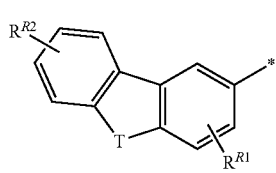

wherein T is selected from O and S, $R^{R1}$ represents one or more optional substituents selected from F, Cl and optionally substituted $C_{1-4}$ alkyl, $C_{1-4}$ alkoxy, $C_{5-7}$ aryl and $C_{5-7}$ aryl-$C_{1-4}$ alkyl, and $R^{R2}$ represents one or more optional substituents selected from F, Cl and optionally substituted $C_{1-4}$ alkyl, $C_{1-4}$ alkoxy, $C_{5-7}$ aryl and $C_{5-7}$ aryl-$C_{1-4}$ alkyl groups;

D is selected from:

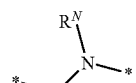

(i)

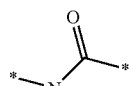

(ii)

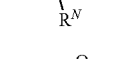

(iii)

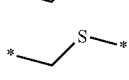

(iv)

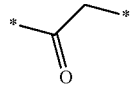

(v)

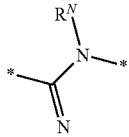

(vi)

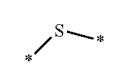

(vii)

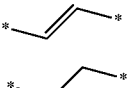

(viii)

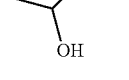

(ix)

B is selected from the group consisting of:

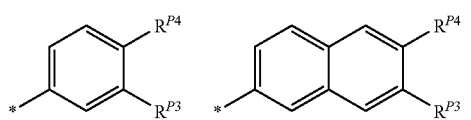

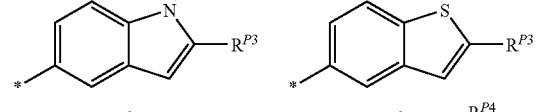

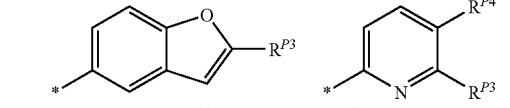

where $R^{N'}$ is selected from H and $C_{1-4}$ alkyl;
where $R^{P6}$ is sleeted from fluoro and chloro;
where one of $R^{P3}$ and $R^{P4}$ is —$C_m$ alkylene-$R^2$ and the other of $R^{P3}$ and $R^{P4}$ is H, m and n can be 0 or 1, and m+n=1 or 2; and additionally when $R^{P3}$ is —$C_m$ alkylene-$R^2$, m can also be 2 or 3, and m+n=1, 2, 3 or 4, and when $R^2$ is tetrazol-5-yl, m+n may be 0;

and where B is selected from the group consisting of:

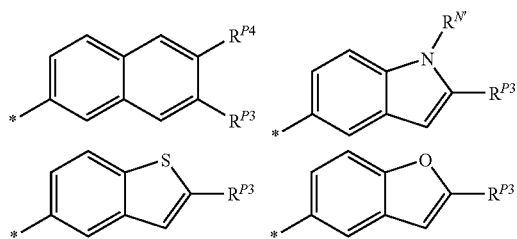

m+n can also equal 0;
or where one of $R^{P3}$ and $R^{P4}$ is —O—CH$_2$—R$^2$, and the other of $R^{P3}$ and $R^{P4}$ is H, n is 0;
$R^N$ is H or optionally substituted $C_{1-4}$ alkyl;
$R^2$ is either:
(i) —CO$_2$H (carboxy);
(ii) —CONH$_2$;
(iii) —CH$_2$—OH; or
(iv) tetrazol-5-yl.

A fifth aspect of the present invention provides a compound of formula (V):

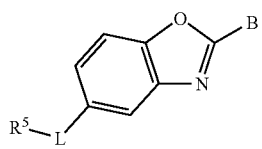

(V)

or a salt, solvate and chemically protected form thereof, wherein:
$R^5$ is an optionally substituted $C_{5-20}$ aryl or $C_{4-20}$ alkyl group;
L' is a single bond, —O— or —C(=O)—;
B is selected from the group consisting of:

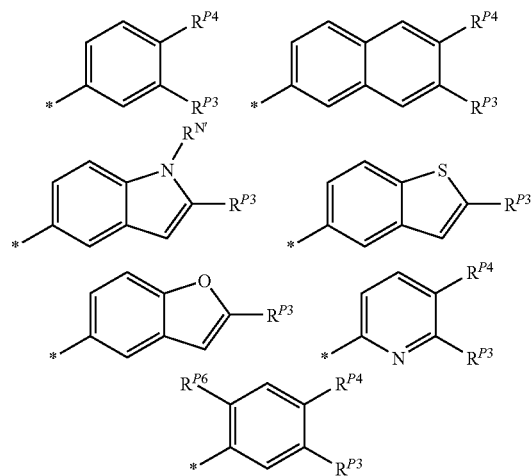

where $R^{N'}$ is selected from H and $C_{1-4}$ alkyl;
where $R^{P6}$ is sleeted from fluoro and chloro;
where one of $R^{P3}$ and $R^{P4}$ is —C$_m$ alkylene-R$^2$ and the other of $R^{P3}$ and $R^{P4}$ is H, m is 1;
and additionally when $R^{P3}$ is —C$_m$ alkylene-R$^2$, m can also be 2 or 3, and when $R^2$ is tetrazol-5-yl, m may be 0; and where B is selected from the group consisting of:

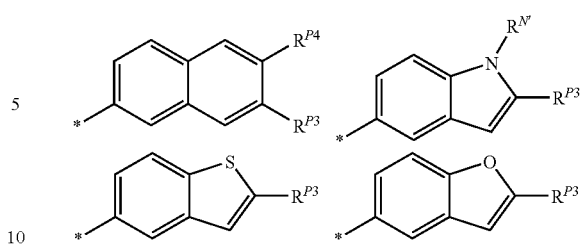

m can also be 0;
or one of $R^{P3}$ and $R^{P4}$ may be —O—CH$_2$—R$^2$, and the other of $R^{P3}$ and $R^{P4}$ is H;
$R^N$ is H or optionally substituted $C_{1-4}$ alkyl;
$R^2$ is either:
(i) —CO$_2$H (carboxy);
(ii) —CONH$_2$;
(iii) —CH$_2$—OH; or
(iv) tetrazol-5-yl.

Therefore, A (where present) may be one of the following groups:

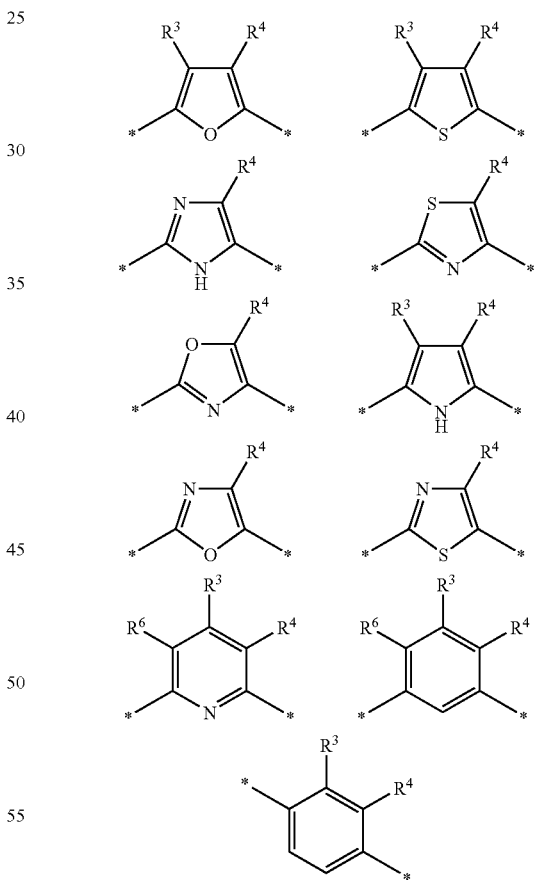

A sixth aspect of the present invention provides a compound of formula (I) to (V) or a pharmaceutically acceptable salt thereof for use in a method of therapy.

A seventh aspect of the present invention provides a pharmaceutical composition comprising a compound of formula (I) to (V) as defined in the first to fifth aspects or a pharmaceutically acceptable salt thereof together with a pharmaceutically acceptable carrier or diluent.

An eighth aspect of the present invention provides the use of a compound of formula (I) to (V) or a pharmaceutically acceptable salt thereof in the preparation of a medicament for the treatment of a condition alleviated by agonism of an $EP_2$ receptor.

A ninth aspect of the present invention provides a method of treating a condition which can be alleviated by agonism of an $EP_2$ receptor, which method comprises administering to a patient in need of treatment an effective amount of a compound of formula (I) to (V), or a pharmaceutically acceptable salt thereof.

In the eighth and ninth aspects of the invention, the agonism of the $EP_2$ receptor may be selective, or may be accompanied by antagonism of the $EP_4$ receptor.

Conditions which can be alleviated by agonism of an $EP_2$ receptor are discussed above, and particularly include dysmenorrhoea, pre-term labour, glaucoma, ocular hypertension, immune disorders, inflammatory disorders, osteoporosis, asthma, chronic obstructive pulmonary disease, allergy, bone disease, fracture repair, male sexual dysfunction, female sexual dysfunction, infertility, periodontal disease, gastric ulcer, renal disease and psoriasis.

Conditions which can be alleviated by combined agonism of $EP_2$ receptors and antagonism of $EP_4$ receptors are discussed above, and particularly include myometrial disorders, bone diseases including osteoporosis and osteoarthritis, allergic and immune disorders such as psoriasis, transplant rejection, and asthma, inflammatory diseases such as rheumatoid arthritis, chronic obstructive pulmonary disease and acute respiratory disease syndrome, and fibrotic lung diseases.

EP receptor agonists are known to be able to inhibit T-cell activation and the release of pro-inflammatory cytokines, although the EP receptor involved in mediating these effects in human T-cells has not been previously defined. Some of the present inventors have discovered that $EP_2$ agonists inhibit human T-cell activation (proliferation) and inhibit the release of multiple pro-inflammatory cytokines including interleukin 2 (IL-2) tumour necrosis factor ($TNF_\alpha$) and interferon gamma (IFNγ), as described in co-pending US and International applications entitled "$EP_2$ Agonists" filed 22 Dec. 2004 in the name of Borman, R. A. et al., (WO 2005/061449), which are herein incorporated by reference. This profile of activity strongly suggests that $EP_2$ receptor agonists will be useful in treating immune and inflammatory disorders, including but not limited to psoriasis, psoriatic arthritis, dermatitis, rheumatoid arthritis, transplant rejection, inflammatory bowel disease, systemic lupus erythematosus, Graves' disease, scleroderma, multiple sclerosis, Type I diabetes, and transplant rejection, and in particular psoriasis (Griffiths, C., *Current Drugs Targets—Inflammation & Allergy*, 3, 157-161, (2004); Lebwohl, M., *Lancet*, 361, 1197-1204 (2003); Salim, A. & Emerson, R., *Curr. Opin. Investig. Drugs*, 2(11), 1546-8 (2001)). Therefore, a further condition which can be alleviated by agonism of an $EP_2$ receptor is psoriasis.

Furthermore, some of the present inventors have also shown that $EP_2$ receptor agonists inhibit the release of the pro-inflammatory cytokine, $TNF_\alpha$ from human monocytes and alveolar macrophages, as described in co-pending US and International applications entitled "$EP_2$ Agonists" filed 22 Dec. 2004 in the name of Borman, R. A. et al., (WO 2005/061449), which are herein incorporated by reference. This profile of activity adds further evidence to the view that that $EP_2$ receptor agonists will be useful in treating immune and inflammatory disorders and in particular, inflammatory lung diseases (including, but not limited to: asthma, chronic obstructive pulmonary disease, acute respiratory distress syndrome, pulmonary fibrosis and cystic fibrosis).

Furthermore, aspects of the present invention relate to the use of $EP_2$ agonists to treat conditions ameliorated by the inhibition of IL-2 $TNF_\alpha$ and/or IFNγ production and the use of an $EP_2$ agonist in the preparation of a medicament for the treatment of a condition alleviated by inhibition of IL-2 production.

The present invention also provides methods of stimulating $EP_2$ receptors and/or inhibiting the production of IL-2, $TNF_\alpha$ and/or IFNγ, in vitro or in vivo, comprising contacting a cell with an effective amount of a compound of the first aspect of the present invention.

Compounds of the present invention can be assayed to determine whether they act as antagonists of an $EP_4$ receptor. Suitable assay methods are described in example 12 below.

The present invention also provides methods of agonising $EP_2$, and possible antagonizing $EP_4$ receptors, in vitro or in vivo, comprising contacting a cell with an effective amount of a compound of formula (I) to (V).

In some embodiments, the compounds described above which function as $EP_2$ agonists may be selective as against modulation of one or more of the other three EP receptors, i.e. $EP_1$, $EP_3$ and $EP_4$. This selectivity allows for targeting of the effect of the compounds of the invention, with possible benefits in the treatment of certain conditions.

Definitions

Monodentate Groups (i.e. Groups with One Point of Covalent Attachment)

Alkyl: The term "alkyl" as used herein, pertains to a monovalent moiety obtained by removing a hydrogen atom from a carbon atom of a hydrocarbon compound having from 1 to 20 carbon atoms (unless otherwise specified), which may be aliphatic or alicyclic, and which may be saturated or unsaturated. Thus, the term "alkyl" includes the sub-classes alkenyl, alkynyl, cycloalkyl, cycloalkenyl, cylcoalkynyl, etc., discussed below.

In the context of alkyl groups, the prefixes (e.g. $C_{1-4}$, $C_{1-7}$, $C_{1-20}$, $C_{2-7}$, $C_{3-7}$) denote the number of carbon atoms, or range of number of carbon atoms. For example, the term "$C_{1-4}$alkyl" as used herein, pertains to an alkyl group having from 1 to 4 carbon atoms. Examples of groups of alkyl groups include $C_{1-4}$ alkyl ("lower alkyl"), $C_{1-17}$ alkyl and $C_{4-20}$ alkyl. Note that the first prefix may vary according to other limitations; for example, for unsaturated alkyl groups, the first prefix must be at least 2; for cyclic alkyl groups, the first prefix must be at least 3; etc.

Examples of saturated alkyl groups include, but are not limited to, methyl ($C_1$), ethyl ($C_2$), propyl ($C_3$), butyl ($C_4$), pentyl ($C_5$), hexyl ($C_6$), heptyl ($C_7$), octyl ($C_8$), nonyl ($C_9$), decyl ($C_{10}$), undecyl ($C_{11}$), dodecyl ($C_{12}$), tridecyl ($C_{13}$), tetradecyl ($C_{14}$), pentadecyl ($C_{15}$), and eicodecyl ($C_{20}$).

Examples of saturated linear alkyl groups include, but are not limited to, methyl ($C_1$), ethyl ($C_2$), n-propyl ($C_3$), n-butyl ($C_4$), n-pentyl (amyl) ($C_5$), n-hexyl ($C_6$), and n-heptyl ($C_7$).

Examples of saturated branched alkyl groups include iso-propyl ($C_3$), iso-butyl ($C_4$), sec-butyl ($C_4$), tert-butyl ($C_4$), iso-pentyl ($C_5$), and neo-pentyl ($C_5$).

Alkenyl: The term "alkenyl" as used herein, pertains to an alkyl group having one or more carbon-carbon double bonds. Examples of alkenyl groups include $C_{2-4}$ alkenyl, $C_{2-7}$ alkenyl and $C_{2-20}$ alkenyl. Examples of alkenyl groups include, but are not limited to, ethenyl (vinyl, —CH=$CH_2$), 1-propenyl (—CH=CH—$CH_3$), 2-propenyl (allyl, —CH—CH=$CH_2$), isopropenyl (1-methylvinyl, —C($CH_3$)=$CH_2$), butenyl ($C_4$), pentenyl ($C_5$), and hexenyl ($C_6$).

Alkynyl: The term "alkynyl" as used herein, pertains to an alkyl group having one or more carbon-carbon triple bonds. Examples of groups of alkynyl groups include $C_{2-4}$ alkynyl, $C_{2-7}$ alkynyl and $C_{2-20}$ alkynyl. Examples of alkynyl groups include, but are not limited to, ethynyl (ethinyl, —C≡CH) and 2-propynyl (propargyl, —CH$_2$—C≡CH).

Cycloalkyl: The term "cycloalkyl" as used herein, pertains to an alkyl group which is also a cyclyl group; that is, a monovalent moiety obtained by removing a hydrogen atom from an alicyclic ring atom of a carbocyclic ring of a carbocyclic compound, which carbocyclic ring may be saturated or unsaturated, which moiety has from 3 to 7 carbon atoms (unless otherwise specified), including from 3 to 7 ring atoms. Thus, the term "cycloalkyl" includes the sub-classes cycloalkenyl and cycloalkynyl. Preferably, each ring has from 3 to 7 ring atoms. Examples of groups of cycloalkyl groups include $C_{3-7}$ cycloalkyl.

Examples of cycloalkyl groups include, but are not limited to, those derived from:

saturated monocyclic hydrocarbon compounds:
cyclopropane ($C_3$), cyclobutane ($C_4$), cyclopentane ($C_5$), cyclohexane ($C_6$), cycloheptane ($C_7$), methylcyclopropane ($C_4$), dimethylcyclopropane ($C_5$), methylcyclobutane ($C_5$), dimethylcyclobutane ($C_6$), methylcyclopentane ($C_6$), dimethylcyclopentane ($C_7$), methylcyclohexane ($C_7$) dimethylcyclohexane ($C_8$), menthane ($C_{10}$);

unsaturated monocyclic hydrocarbon compounds:
cyclopropene ($C_3$), cyclobutene ($C_4$), cyclopentene ($C_5$), cyclohexene ($C_6$), methylcyclopropene ($C_4$), dimethylcyclopropene ($C_5$), methylcyclobutene ($C_5$), dimethylcyclobutene ($C_6$), methylcyclopentene ($C_6$), dimethylcyclopentene ($C_7$), methylcyclohexene ($C_7$) dimethylcyclohexene ($C_8$);

saturated polycyclic hydrocarbon compounds:
thujane ($C_{10}$), carane ($C_{10}$), pinane ($C_{10}$), bornane ($C_{10}$), norcarane ($C_7$), norpinane ($C_7$), norbornane ($C_7$), adamantane ($C_{10}$), decalin (decahydronaphthalene) ($C_{10}$);

unsaturated polycyclic hydrocarbon compounds:
camphene ($C_{10}$), limonene ($C_{10}$), pinene ($C_{10}$).

Heterocyclyl: The term "heterocyclyl" as used herein, pertains to a monovalent moiety obtained by removing a hydrogen atom from a ring atom of a heterocyclic compound, which moiety has from 3 to 20 ring atoms (unless otherwise specified), of which from 1 to 10 are ring heteroatoms. Preferably, each ring has from 3 to 7 ring atoms, of which from 1 to 4 are ring heteroatoms.

In this context, the prefixes (e.g. $C_{3-20}$, $C_{3-7}$, $C_{5-6}$, etc.) denote the number of ring atoms, or range of number of ring atoms, whether carbon atoms or heteroatoms. For example, the term "$C_{5-6}$ heterocyclyl" as used herein, pertains to a heterocyclyl group having 5 or 6 ring atoms. Examples of groups of heterocyclyl groups include $C_{3-20}$ heterocyclyl, $C_{5-20}$ heterocyclyl, $C_{3-15}$ heterocyclyl, $C_{5-15}$ heterocyclyl, $C_{3-12}$ heterocyclyl, $C_{5-12}$ heterocyclyl, $C_{3-10}$ heterocyclyl, $C_{5-10}$ heterocyclyl, $C_{3-7}$ heterocyclyl, $C_{5-7}$ heterocyclyl, and $C_{5-6}$ heterocyclyl.

Examples of monocyclic heterocyclyl groups include, but are not limited to, those derived from:

$N_1$: aziridine ($C_3$), azetidine ($C_4$), pyrrolidine (tetrahydropyrrole) ($C_5$), pyrroline (e.g., 3-pyrroline, 2,5-dihydropyrrole) ($C_5$), 2H-pyrrole or 3H-pyrrole (isopyrrole, isoazole) ($C_5$), piperidine ($C_6$), dihydropyridine ($C_6$), tetrahydropyridine ($C_6$), azepine ($C_7$);

$O_1$: oxirane ($C_3$), oxetane ($C_4$), oxolane (tetrahydrofuran) ($C_5$), oxole (dihydrofuran) ($C_5$), oxane (tetrahydropyran) ($C_6$), dihydropyran ($C_6$), pyran ($C_6$), oxepin ($C_7$);

$S_1$: thiirane ($C_3$), thietane ($C_4$), thiolane (tetrahydrothiophene) ($C_5$), thiane (tetrahydrothiopyran) ($C_6$), thiepane ($C_7$);

$O_2$: dioxolane ($C_5$), dioxane ($C_6$), and dioxepane ($C_7$);

$O_3$: trioxane ($C_6$);

$N_2$: imidazolidine ($C_5$), pyrazolidine (diazolidine) ($C_5$), imidazoline ($C_5$), pyrazoline (dihydropyrazole) ($C_5$), piperazine ($C_6$);

$N_1O_1$: tetrahydrooxazole ($C_5$), dihydrooxazole ($C_5$), tetrahydroisoxazole ($C_5$), dihydroisoxazole ($C_5$), morpholine ($C_6$), tetrahydrooxazine ($C_6$), dihydrooxazine ($C_6$), oxazine ($C_6$);

$N_1S_1$: thiazoline ($C_5$), thiazolidine ($C_5$), thiomorpholine ($C_6$);

$N_2O_1$: oxadiazine ($C_6$);

$O_1S_1$: oxathiole ($C_5$) and oxathiane (thioxane) ($C_6$); and, $N_1O_1S_1$: oxathiazine ($C_6$).

Aryl: The term "aryl" as used herein, pertains to a monovalent moiety obtained by removing a hydrogen atom from an aromatic ring atom of an aromatic compound, which moiety has from 3 to 20 ring atoms (unless otherwise specified). Preferably, each ring has from 5 to 7 ring atoms.

In this context, the prefixes (e.g. $C_{3-20}$, $C_{5-7}$, $C_{5-6}$, etc.) denote the number of ring atoms, or range of number of ring atoms, whether carbon atoms or heteroatoms. For example, the term "$C_{5-6}$ aryl" as used herein, pertains to an aryl group having 5 or 6 ring atoms. Examples of groups of aryl groups include $C_{3-20}$ aryl, $C_{5-20}$ aryl, $C_{5-15}$ aryl, $C_{5-12}$ aryl, $C_{5-10}$ aryl, $C_{5-7}$ aryl, $C_{5-6}$ aryl, $C_5$ aryl, and $C_6$ aryl.

The ring atoms may be all carbon atoms, as in "carboaryl groups". Examples of carboaryl groups include $C_{3-20}$ carboaryl, $C_{5-20}$ carboaryl, $C_{5-15}$ carboaryl, $C_{5-12}$ carboaryl, $C_{5-10}$ carboaryl, $C_{5-7}$ carboaryl, $C_{5-6}$ carboaryl, $C_5$ carboaryl, and $C_6$ carboaryl.

Examples of carboaryl groups include, but are not limited to, those derived from benzene (i.e. phenyl) ($C_6$), naphthalene ($C_{10}$), azulene ($C_{10}$), anthracene ($C_{14}$), phenanthrene ($C_{14}$), naphthacene ($C_{18}$), and pyrene ($C_{16}$).

Examples of aryl groups which comprise fused rings, at least one of which is an aromatic ring, include, but are not limited to, groups derived from indane (e.g., 2,3-dihydro-1H-indene) ($C_9$), indene ($C_9$), isoindene ($C_9$), tetraline (1,2,3,4-tetrahydronaphthalene ($C_{10}$), acenaphthene ($C_{12}$), fluorene ($C_{13}$), phenalene ($C_{13}$), acephenanthrene ($C_{15}$), and aceanthrene ($C_{16}$).

Alternatively, the ring atoms may include one or more heteroatoms, as in "heteroaryl groups". Examples of heteroaryl groups include $C_{3-20}$ heteroaryl, $C_{5-20}$ heteroaryl, $C_{5-15}$ heteroaryl, $C_{5-12}$ heteroaryl, $C_{5-10}$ heteroaryl, $C_{5-7}$ heteroaryl, $C_{5-6}$ heteroaryl, $C_6$ heteroaryl, and $C_5$ heteroaryl.

Examples of monocyclic heteroaryl groups include, but are not limited to, those derived from:

$N_1$: pyrrole (azole) ($C_6$), pyridine (azine) ($C_6$);

$O_1$: furan (oxole) ($C_5$);

$S_1$: thiophene (thiole) ($C_5$);

$N_1O_1$: oxazole ($C_5$), isoxazole ($C_5$), isoxazine ($C_6$);

$N_2O_1$: oxadiazole (furazan) ($C_5$);

$N_3O_1$: oxatriazole ($C_5$);

$N_1S_1$: thiazole ($C_5$), isothiazole ($C_5$);

$N_2$: imidazole (1,3-diazole) ($C_5$), pyrazole (1,2-diazole) ($C_5$), pyridazine (1,2-diazine) ($C_6$), pyrimidine (1,3-diazine) ($C_6$), pyrazine (1,4-diazine) ($C_6$);

$N_3$: triazole ($C_5$), triazine ($C_6$); and, $N_4$: tetrazole ($C_5$).

Examples of heteroaryl groups which comprise fused rings, include, but are not limited to:

$C_9$ (with 2 fused rings) derived from benzofuran ($O_1$), isobenzofuran ($O_1$), indole ($N_1$), isoindole ($N_1$), indolizine ($N_1$), indoline ($N_1$), isoindoline ($N_1$), purine ($N_4$) (e.g., adenine, guanine), benzimidazole ($N_2$), indazole ($N_2$), benzoxazole ($N_1O_1$), benzisoxazole ($N_1O_1$), benzodioxole ($O_2$), benzofurazan ($N_2O_1$), benzotriazole ($N_3$), benzothiofuran ($S_1$), benzothiazole ($N_1S_1$), benzothiadiazole ($N_2S$);

$C_{10}$ (with 2 fused rings) derived from chromene ($O_1$), isochromene ($O_1$), chroman ($O_1$), isochroman ($O_1$), benzodioxan ($O_2$), quinoline ($N_1$), isoquinoline ($N_1$), quinolizine ($N_1$), benzoxazine ($N_1O_1$), benzodiazine ($N_2$), pyridopyridine ($N_2$), quinoxaline ($N_2$), quinazoline ($N_2$), cinnoline ($N_2$), phthalazine ($N_2$), naphthyridine ($N_2$), pteridine ($N_4$);

$C_{11}$ (with 2 fused rings) derived from benzodiazepine ($N_2$);

$C_{13}$ (with 3 fused rings) derived from carbazole ($N_1$), dibenzofuran ($O_1$), dibenzothiophene ($S_1$), carboline ($N_2$), perimidine ($N_2$), pyridoindole ($N_2$); and, $C_{14}$ (with 3 fused rings) derived from acridine ($N_1$), xanthene ($O_1$), thioxanthene ($S_1$), oxanthrene ($O_2$), phenoxathiin ($O_1S_1$), phenazine ($N_2$), phenoxazine ($N_1O_1$), phenothiazine ($N_1S_1$), thianthrene ($S_2$), phenanthridine ($N_1$), phenanthroline ($N_2$), phenazine ($N_2$).

If a heteroaryl or heterocyclyl group contains a nitrogen ring atom, this ring atom, where possible, may be in a oxidised state, as an N-oxide.

The above groups, whether alone or part of another substituent, may themselves optionally be substituted with one or more groups selected from themselves, the additional monodentate substituents listed below and alkoxylene.

Halo: —F, —Cl, —Br, and —I.
Hydroxy: —OH.
Ether: —OR, wherein R is an ether substituent, for example, a $C_{1-7}$ alkyl group (also referred to as a $C_{1-7}$alkoxy group, discussed below), a $C_{3-20}$ heterocyclyl group (also referred to as a $C_{3-20}$ heterocyclyloxy group), or a $C_{5-20}$ aryl group (also referred to as a $C_{5-20}$ aryloxy group), preferably a $C_{1-7}$ alkyl group.

$C_{1-7}$alkoxy: —OR, wherein R is a $C_{1-7}$ alkyl group. Examples of $C_{1-7}$alkoxy groups include, but are not limited to, —OMe (methoxy), —OEt (ethoxy), —O(nPr) (n-propoxy), —O(iPr) (isopropoxy), —O(nBu) (n-butoxy), —O(sBu) (sec-butoxy), —O(iBu) (isobutoxy), and —O(tBu) (tert-butoxy).

Oxo (keto, -one): =O.
Thione (thioketone): =S.
Imino (imine): =NR, wherein R is an imino substituent, for example, hydrogen, $C_{1-7}$ alkyl group, a $C_{3-20}$heterocyclyl group, or a $C_{5-20}$ aryl group, preferably hydrogen or a $C_{1-7}$ alkyl group. Examples of imino groups include, but are not limited to, =NH, =NMe, =NEt, and =NPh.

Formyl (carbaldehyde, carboxaldehyde): —C(=O)H.
Acyl (keto): —C(=O)R, wherein R is an acyl substituent, for example, a $C_{1-7}$ alkyl group (also referred to as $C_{1-7}$ alkylacyl or $C_{1-7}$ alkanoyl), a $C_{3-20}$ heterocyclyl group (also referred to as $C_{3-20}$ heterocyclylacyl), or a $C_{5-20}$ aryl group (also referred to as $C_{5-20}$ arylacyl), preferably a $C_{1-7}$ alkyl group. Examples of acyl groups include, but are not limited to, —C(=O)$CH_3$ (acetyl), —C(=O)$CH_2CH_3$ (propionyl), —C(=O)C($CH_3$)$_3$ (t-butyryl), and —C(=O)Ph (benzoyl, phenone).

Carboxy (carboxylic acid): —C(=O)OH.
Thiocarboxy (thiocarboxylic acid): —C(=S)SH.
Thiolocarboxy (thiolocarboxylic acid): —C(=O)SH.
Thionocarboxy (thionocarboxylic acid): —C(=S)OH.
Imidic acid: —C(=NH)OH.
Hydroxamic acid: —C(=NOH)OH.
Ester (carboxylate, carboxylic acid ester, oxycarbonyl): —C(=O)OR, wherein R is an ester substituent, for example, a $C_{1-7}$ alkyl group, a $C_{3-20}$ heterocyclyl group, or a $C_{5-20}$ aryl group, preferably a $C_{1-7}$ alkyl group. Examples of ester groups include, but are not limited to, —C(=O)O$CH_3$, —C(=O)O$CH_2CH_3$, —C(=O)OC($CH_3$)$_3$, and —C(=O)OPh.

Acyloxy (reverse ester): —OC(=O)R, wherein R is an acyloxy substituent, for example, a $C_{1-7}$ alkyl group, a $C_{3-20}$ heterocyclyl group, or a $C_{5-20}$ aryl group, preferably a $C_{1-7}$ alkyl group. Examples of acyloxy groups include, but are not limited to, —OC(=O)$CH_3$ (acetoxy), —OC(=O)$CH_2CH_3$, —OC(=O)C($CH_3$)$_3$, —OC(=O)Ph, and —OC(=O)$CH_2$Ph.

Amido (carbamoyl, carbamyl, aminocarbonyl, carboxamide): —C(=O)$NR^1R^2$, wherein $R^1$ and $R^2$ are independently amino substituents, as defined for amino groups. Examples of amido groups include, but are not limited to, —C(=O)$NH_2$, —C(=O)$NHCH_3$, —C(=O)N($CH_3$)$_2$, —C(=O)$NHCH_2CH_3$, and —C(=O)N($CH_2CH_3$)$_2$, as well as amido groups in which $R^1$ and $R^2$, together with the nitrogen atom to which they are attached, form a heterocyclic structure as in, for example, piperidinocarbonyl, morpholinocarbonyl, thiomorpholinocarbonyl, and piperazinocarbonyl.

Acylamino: —$NR^1$C(=O)$R^2$, wherein $R^1$ is an amide substituent, for example, hydrogen, a $C_{1-7}$ alkyl group, a $C_{3-20}$ heterocyclyl group, or a $C_{5-20}$aryl group, preferably hydrogen or a $C_{1-7}$ alkyl group, and $R^2$ is an acyl substituent, for example, a $C_{1-7}$ alkyl group, a $C_{3-20}$ heterocyclyl group, or a $C_{5-20}$ aryl group, preferably hydrogen or a $C_{1-7}$ alkyl group. Examples of acylamide groups include, but are not limited to, —NHC(=O)$CH_3$, —NHC(=O)$CH_2CH_3$, and —NHC(=O)Ph. $R^1$ and $R^2$ may together form a cyclic structure, as in, for example, succinimidyl, maleimidyl, and phthalimidyl:

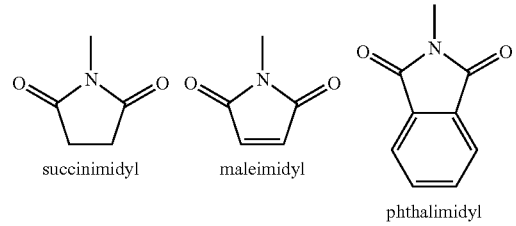

succinimidyl    maleimidyl    phthalimidyl

Thioamido (thiocarbamyl): —C(=S)$NR^1R^2$, wherein $R^1$ and $R^2$ are independently amino substituents, as defined for amino groups. Examples of thioamido groups include, but are not limited to, —C(=S)$NH_2$, —C(=S)$NHCH_3$, —C(=S)N($CH_3$)$_2$, and —C(=S)$NHCH_2CH_3$.

Ureido: —N($R^1$)CON$R^2R^3$ wherein $R^2$ and $R^3$ are independently amino substituents, as defined for amino groups, and $R^1$ is a ureido substituent, for example, hydrogen, a $C_{1-7}$ alkyl group, a $C_{3-20}$ heterocyclyl group, or a $O_{5-20}$ aryl group, preferably hydrogen or a $C_{1-7}$ alkyl group. Examples of ureido groups include, but are not limited to, —NHCON$H_2$, —NHCONHMe, —NHCONHEt, —NHCONMe$_2$, —NHCONEt$_2$, —NMeCONH$_2$, —NMeCONHMe, —NMeCONHEt, —NMeCONMe$_2$, and —NMeCONEt$_2$.

Guanidino: —NH—C(=NH)$NH_2$.
Tetrazolyl: a five membered aromatic ring having four nitrogen atoms and one carbon atom,

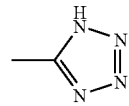

Amino: —NR$^1$R$^2$, wherein R$^1$ and R$^2$ are independently amino substituents, for example, hydrogen, a C$_{1-7}$ alkyl group (also referred to as C$_{1-7}$ alkylamino or di-C$_{1-7}$ alkylamino), a C$_{3-20}$ heterocyclyl group, or a C$_{5-20}$aryl group, preferably H or a C$_{1-7}$ alkyl group, or, in the case of a "cyclic" amino group, R$^1$ and R$^2$, taken together with the nitrogen atom to which they are attached, form a heterocyclic ring having from 4 to 8 ring atoms. Amino groups may be primary (—NH$_2$), secondary (—NHR$^1$), or tertiary (—NHR$^1$R$^2$), and in cationic form, may be quaternary (—$^+$NR$^1$R$^2$R$^3$). Examples of amino groups include, but are not limited to, —NH$_2$, —NHCH$_3$, —NHC(CH$_3$)$_2$, —N(CH$_3$)$_2$, —N(CH$_2$CH$_3$)$_2$, and —NHPh. Examples of cyclic amino groups include, but are not limited to, aziridino, azetidino, pyrrolidino, piperidino, piperazino, morpholino, and thiomorpholino.

Amidine (amidino): —C(=NR)NR$_2$, wherein each R is an amidine substituent, for example, hydrogen, a C$_{1-7}$ alkyl group, a C$_{3-20}$ heterocyclyl group, or a C$_{5-20}$ aryl group, preferably H or a C$_{1-7}$ alkyl group. Examples of amidine groups include, but are not limited to, —C(=NH)NH$_2$, —C(=NH)NMe$_2$, and —C(=NMe)NMe$_2$.

Nitro: —NO$_2$.
Nitroso: —NO.
Cyano (nitrile, carbonitrile): —CN.
Sulfhydryl (thiol, mercapto): —SH.

Thioether (sulfide): —SR, wherein R is a thioether substituent, for example, a C$_{1-7}$ alkyl group (also referred to as a C$_{1-7}$ alkylthio group), a C$_{3-20}$ heterocyclyl group, or a C$_{5-20}$ aryl group, preferably a C$_{1-7}$ alkyl group. Examples of C$_{1-7}$alkylthio groups include, but are not limited to, —SCH$_3$ and —SCH$_2$CH$_3$.

Disulfide: —SS—R, wherein R is a disulfide substituent, for example, a C$_{1-7}$ alkyl group, a C$_{3-20}$ heterocyclyl group, or a C$_{5-20}$ aryl group, preferably a C$_{1-7}$ alkyl group (also referred to herein as C$_{1-7}$ alkyl disulfide). Examples of C$_{1-7}$ alkyl disulfide groups include, but are not limited to, —SSCH$_3$ and —SSCH$_2$CH$_3$.

Sulfine (sulfinyl, sulfoxide): —S(=O)R, wherein R is a sulfine substituent, for example, a C$_{1-7}$ alkyl group, a C$_{3-20}$ heterocyclyl group, or a C$_{5-20}$ aryl group, preferably a C$_{1-7}$ alkyl group. Examples of sulfine groups include, but are not limited to, —S(=O)CH$_3$ and —S(=O)CH$_2$CH$_3$.

Sulfone (sulfonyl): —S(=O)$_2$R, wherein R is a sulfone substituent, for example, a C$_{1-7}$ alkyl group, a C$_{3-20}$ heterocyclyl group, or a C$_{5-20}$ aryl group, preferably a C$_{1-7}$ alkyl group, including, for example, a fluorinated or perfluorinated C$_{1-7}$ alkyl group. Examples of sulfone groups include, but are not limited to, —S(=O)$_2$CH$_3$ (methanesulfonyl, mesyl), —S(=O)$_2$CF$_3$ (triflyl), —S(=O)$_2$CH$_2$CH$_3$ (esyl), —S(=O)$_2$C$_4$F$_9$ (nonaflyl), —S(=O)$_2$CH$_2$CF$_3$ (tresyl), —S(=O)$_2$CH$_2$CH$_2$NH$_2$ (tauryl), —S(=O)$_2$Ph (phenylsulfonyl, besyl), 4-methylphenylsulfonyl (tosyl), 4-chlorophenylsulfonyl (closyl), 4-bromophenylsulfonyl (brosyl), 4-nitrophenyl (nosyl), 2-naphthalenesulfonate (napsyl), and 5-dimethylamino-naphthalen-1-ylsulfonate (dansyl).

Sulfinic acid (sulfino): —S(=O)OH, —SO$_2$H.
Sulfonic acid (sulfo): —S(=O)$_2$OH, —SO$_3$H.

Sulfinate (sulfinic acid ester): —S(=O)OR; wherein R is a sulfinate substituent, for example, a C$_{1-7}$ alkyl group, a C$_{3-20}$ heterocyclyl group, or a C$_{5-20}$ aryl group, preferably a C$_{1-7}$ alkyl group. Examples of sulfinate groups include, but are not limited to, —S(=O)OCH$_3$ (methoxysulfinyl; methyl sulfinate) and —S(=O)OCH$_2$CH$_3$ (ethoxysulfinyl; ethyl sulfinate).

Sulfinyloxy: —OS(=O)R, wherein R is a sulfinyloxy substituent, for example, a C$_{1-7}$ alkyl group, a C$_{3-20}$ heterocyclyl group, or a C$_{6-20}$ aryl group, preferably a C$_{1-7}$ alkyl group.

Examples of sulfinyloxy groups include, but are not limited to, —OS(=O)CH$_3$ and —OS(=O)CH$_2$CH$_3$.

Sulfamyl (sulfamoyl; sulfinic acid amide; sulfinamide): —S(=O)NR$^1$R$^2$, wherein R$^1$ and R$^2$ are independently amino substituents, as defined for amino groups. Examples of sulfamyl groups include, but are not limited to, —S(=O)NH$_2$, —S(=O)NH(CH$_3$), —S(=O)N(CH$_3$)$_2$, —S(=O)NH(CH$_2$CH$_3$), —S(=O)N(CH$_2$CH$_3$)$_2$, and —S(=O)NHPh.

Sulfonamido (sulfinamoyl; sulfonic acid amide; sulfonamide): —S(=O)$_2$NR$^1$R$^2$, wherein R$^1$ and R$^2$ are independently amino substituents, as defined for amino groups. Examples of sulfonamido groups include, but are not limited to, —S(=O)$_2$NH$_2$, —S(=O)$_2$NH(CH$_3$), —S(=O)$_2$N(CH$_3$)$_2$, —S(=O)$_2$NH(CH$_2$CH$_3$), —S(=O)$_2$N(CH$_2$CH$_3$)$_2$, and —S(=O)$_2$NHPh.

Sulfonamino: —NR$^1$S(=O)$_2$R, wherein R$^1$ is an amino substituent, as defined for amino groups, and R is a sulfonamino substituent, for example, a C$_{1-7}$ alkyl group, a C$_{3-20}$ heterocyclyl group, or a C$_{5-20}$ aryl group, preferably a alkyl group. Examples of sulfonamino groups include, but are not limited to, —NHS(=O)$_2$CH$_3$ and —N(CH$_3$)S(=O)$_2$C$_6$H$_5$.

Sulfinamino: —NR$^1$S(=O)R, wherein R$^1$ is an amino substituent, as defined for amino groups, and R is a sulfinamino substituent, for example, a C$_{1-7}$ alkyl group, a C$_{3-20}$ heterocyclyl group, or a C$_{5-20}$ aryl group, preferably a C$_{1-7}$ alkyl group. Examples of sulfinamino groups include, but are not limited to, —NHS(=O)CH$_3$ and —N(CH$_3$)S(=O)C$_6$H$_5$.

As already mentioned, the above described groups may be substituted, and particular examples include, but are not limited to, C$_{3-20}$ aryl-C$_{1-7}$ alkyl groups, which include benzyl (phenylmethyl, PhCH$_2$—), benzhydryl (Ph$_2$CH—), trityl (triphenylmethyl, Ph$_3$C—), phenethyl (phenylethyl, Ph-CH$_2$CH$_2$—), styryl (Ph-CH=CH—) and cinnamyl (Ph-CH=CH—CH$_2$—).

Bidentate Groups
(i.e. Groups with Two Points of Covalent Attachment; Linking Groups)

Alkylene: The term "C$_{1-3}$ alkylene", as used herein, pertains to a bidentate moiety obtained by removing two hydrogen atoms from each of two different carbon atoms, of a linear hydrocarbon compound having from 1 to 3 carbon atoms, which may be saturated or unsaturated. Thus, the term "alkylene" includes the sub-classes alkenylene and alkynylene.

In this context, the prefix C$_{1-3}$ denotes the number of carbon atoms, or range of number of carbon atoms.

Examples of saturated C$_{1-3}$alkylene groups include —CH$_2$— (methylene), —CH$_2$CH$_2$-(ethylene) and —CH$_2$CH$_2$CH$_2$— (propylene).

Examples of unsaturated C$_{1-3}$ alkylene groups (which may be termed "C$_{2-3}$ alkenylene" or "C$_{2-3}$ alkynylene", as appropriate) include —CH=CH— (vinylene), —CH=CH—CH$_2$—, —CH$_2$—CH=CH—, —C≡C—, —C≡C—CH$_2$— and —CH$_2$—C≡C—.

The C$_{1-3}$ alkylene group may be substituted by any monodentate substituent described above.

Alkoxylene: The term "alkoxylene," as used herein, pertains to a bidentate group of formula —O(CH$_2$)$_n$—O—, where n is 1 or 2.

Includes Other Forms

Unless otherwise specified, included in the above are the well known ionic, salt, solvate, and protected forms of these substituents. For example, a reference to carboxylic acid (—COOH) also includes the anionic (carboxylate) form (—COO$^-$), a salt or solvate thereof, as well as conventional protected forms. Similarly, a reference to an amino group includes the protonated form (—N$^+$HR$^1$R$^2$), a salt or solvate of the amino group, for example, a hydrochloride salt, as well as conventional protected forms of an amino group. Similarly, a reference to a hydroxyl group also includes the anionic form (—O⁻), a salt or solvate thereof, as well as conventional protected forms of a hydroxyl group.

Isomers, Salts, Solvates and Protected Forms

Certain compounds may exist in one or more particular geometric, optical, enantiomeric, diasteriomeric, epimeric, stereoisomeric, tautomeric, conformational, or anomeric forms, including but not limited to, cis- and trans-forms; E- and Z-forms; c-, t-, and r-forms; endo- and exo-forms; R-, S-, and meso-forms; O- and L-forms; d- and l-forms; (+) and (−) forms; keto-, enol-, and enolate-forms; syn- and anti-forms; synclinal- and anticlinal-forms; α- and β-forms; axial and equatorial forms; boat-, chair-, twist-, envelope-, and halfchair-forms; and combinations thereof, hereinafter collectively referred to as "isomers" (or "isomeric forms").

Note that, except as discussed below for tautomeric forms, specifically excluded from the term "isomers", as used herein, are structural (or constitutional) isomers (i.e. isomers which differ in the connections between atoms rather than merely by the position of atoms in space). For example, a reference to a methoxy group, —OCH₃, is not to be construed as a reference to its structural isomer, a hydroxymethyl group, —CH₂OH. Similarly, a reference to ortho-chlorophenyl is not to be construed as a reference to its structural isomer, meta-chlorophenyl. However, a reference to a class of structures may well include structurally isomeric forms falling within that class (e.g. $C_{1-7}$alkyl includes n-propyl and iso-propyl; butyl includes n-, iso-, sec-, and tea-butyl; methoxyphenyl includes ortho-, meta-, and para-methoxyphenyl).

The above exclusion does not pertain to tautomeric forms, for example, keto-, enol-, and enolate-forms, as in, for example, the following tautomeric pairs: keto/enol (illustrated below), imine/enamine, amide/imino alcohol, amidine/amidine, nitroso/oxime, thioketone/enethiol, N-nitroso/hyroxyazo, and nitro/aci-nitro.

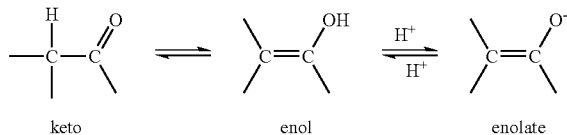

keto          enol          enolate

Note that specifically included in the term "isomer" are compounds with one or more isotopic substitutions. For example, H may be in any isotopic form, including ¹H, ²H (D), and ³H (T); C may be in any isotopic form, including ¹²C, ¹³C, and ¹⁴C; O may be in any isotopic form, including ¹⁶O and ¹⁸O; and the like.

Unless otherwise specified, a reference to a particular compound includes all such isomeric forms, including (wholly or partially) racemic and other mixtures thereof. Methods for the preparation (e.g. asymmetric synthesis) and separation (e.g. fractional crystallisation and chromatographic means) of such isomeric forms are either known in the art or are readily obtained by adapting the methods taught herein, or known methods, in a known manner.

Unless otherwise specified, a reference to a particular compound also includes ionic, salt, solvate, and protected forms of thereof, for example, as discussed below.

It may be convenient or desirable to prepare, purify, and/or handle a corresponding salt of the active compound, for example, a pharmaceutically-acceptable salt. Examples of pharmaceutically acceptable salts are discussed in Berge, et al., *J. Pharm. Sci.*, 66, 1-19 (1977).

For example, if the compound is anionic, or has a functional group which may be anionic (e.g. —COOH may be —COO⁻), then a salt may be formed with a suitable cation. Examples of suitable inorganic cations include, but are not limited to, alkali metal ions such as Na⁺ and K⁺, alkaline earth cations such as Ca²⁺ and Mg²⁺, and other cations such as Al³⁺. Examples of suitable organic cations include, but are not limited to, ammonium ion (i.e. NH₄⁺) and substituted ammonium ions (e.g. NH₃R⁺, NH₂R₂⁺, NHR₃⁺, NR₄⁺). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is N(CH₃)₄⁺.

If the compound is cationic, or has a functional group which may be cationic (e.g. —NH₂ may be —NH₃⁺), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous.

Examples of suitable organic anions include, but are not limited to, those derived from the following organic acids: 2-acetyoxybenzoic, acetic, ascorbic, aspartic, benzoic, camphorsulfonic, cinnamic, citric, edetic, ethanedisulfonic, ethanesulfonic, fumaric, glucoheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, and valeric. Examples of suitable polymeric organic anions include, but are not limited to, those derived from the following polymeric acids: tannic acid, carboxymethyl cellulose.

It may be convenient or desirable to prepare, purify, and/or handle a corresponding solvate of the active compound. The term "solvate" is used herein in the conventional sense to refer to a complex of solute (e.g., active compound, salt of active compound) and solvent. If the solvent is water, the solvate may be conveniently referred to as a hydrate, for example, a mono-hydrate, a di-hydrate, a tri-hydrate, etc.

It may be convenient or desirable to prepare, purify, and/or handle the active compound in a chemically protected form. The term "chemically protected form" is used herein in the conventional chemical sense and pertains to a compound in which one or more reactive functional groups are protected from undesirable chemical reactions under specified conditions (e.g. pH, temperature, radiation, solvent, and the like). In practice, well known chemical methods are employed to reversibly render unreactive a functional group, which otherwise would be reactive, under specified conditions. In a chemically protected form, one or more reactive functional groups are in the form of a protected or protecting group (also known as a masked or masking group or a blocked or blocking group). By protecting a reactive functional group, reactions involving other unprotected reactive functional groups can be performed, without affecting the protected group; the protecting group may be removed, usually in a subsequent step, without substantially affecting the remainder of the molecule. See, for example, *Protective Groups in Organic Synthesis* (T. Green and P. Wuts; 3rd Edition; John Wiley and Sons, 1999).

A wide variety of such "protecting", "blocking", or "masking" methods are widely used and well known in organic synthesis. For example, a compound which has two non-equivalent reactive functional groups, both of which would be reactive under specified conditions, may be derivatized to render one of the functional groups "protected," and therefore unreactive, under the specified conditions; so protected, the compound may be used as a reactant which has effectively only one reactive functional group. After the desired reaction (involving the other functional group) is complete, the protected group may be "deprotected" to return it to its original functionality.

For example, a hydroxy group may be protected as an ether (—OR) or an ester (—OC(=O)R), for example, as: a t-butyl ether; a benzyl, benzhydryl (diphenylmethyl), or trityl (triphenylmethyl)ether; a trimethylsilyl or t-butyldimethylsilyl ether; or an acetyl ester (—OC(=O)CH$_3$, —OAc).

For example, an aldehyde or ketone group may be protected as an acetal (R—CH(OR)$_2$) or ketal (R$_2$C(OR)$_2$), respectively, in which the carbonyl group (>C=O) is converted to a diether (>C(OR)$_2$), by reaction with, for example, a primary alcohol. The aldehyde or ketone group is readily regenerated by hydrolysis using a large excess of water in the presence of acid.

For example, an amine group may be protected, for example, as an amide (—NRCO—R) or a urethane (—NRCO—OR), for example, as: an acetamide (—NHCO—CH$_3$); a benzyloxy amide (—NHCO—OCH$_2$C$_6$H$_5$, —NH-Cbz); as a t-butoxy amide (—NHCO—OC(CH$_3$)$_3$, —NH-Boc); a 2-biphenyl-2-propoxy amide (—NHCO—OC(CH$_3$)$_2$C$_6$H$_4$C$_6$H$_5$, —NH-Bpoc), as a 9-fluorenylmethoxy amide (—NH-Fmoc), as a 6-nitroveratryloxy amide (—NH-Nvoc), as a 2-trimethylsilylethyloxy amide (—NH-Teoc), as a 2,2,2-trichloroethyloxy amide (—NH-Troc), as an allyloxy amide (—NH-Alloc), as a 2(-phenylsulfonyl)ethyloxy amide (—NH-Psec); or, in suitable cases (e.g., cyclic amines), as a nitroxide radical (>N—O.).

For example, a carboxylic acid group may be protected as an ester for example, as: an C$_{1-7}$ alkyl ester (e.g., a methyl ester; a t-butyl ester); a C$_{1-7}$ haloalkyl ester (e.g., a C$_{1-7}$ trihaloalkyl ester); a triC$_{1-7}$ alkylsilyl-C$_{1-7}$ alkyl ester; or a C$_{5-20}$ aryl-C$_{1-7}$ alkyl ester (e.g. a benzyl ester; a nitrobenzyl ester); or as an amide, for example, as a methyl amide.

For example, a thiol group may be protected as a thioether (—SR), for example, as: a benzyl thioether; an acetamidomethyl ether (—S—CH$_2$NHC(=O)CH$_3$).

The term "treatment", as used herein in the context of treating a condition, pertains generally to treatment and therapy, whether of a human or an animal (e.g. in veterinary applications), in which some desired therapeutic effect is achieved, for example, the inhibition of the progress of the condition, and includes a reduction in the rate of progress, a halt in the rate of progress, amelioration of the condition, and cure of the condition. Treatment as a prophylactic measure (i.e. prophylaxis) is also included.

The term "therapeutically-effective amount", as used herein, pertains to that amount of an active compound, or a material, composition or dosage form comprising an active compound, which is effective for producing some desired therapeutic effect, commensurate with a reasonable benefit/risk ratio, when administered in accordance with a desired treatment regimen. Suitable dose ranges will typically be in the range of from 0.01 to 20 mg/kg/day, preferably from 0.1 to 10 mg/kg/day.

Compositions and their Administration

Compositions may be formulated for any suitable route and means of administration. Pharmaceutically acceptable carriers or diluents include those used in formulations suitable for oral, rectal, nasal, topical (including buccal and sublingual), vaginal or parenteral (including subcutaneous, intramuscular, intravenous, intradermal, intrathecal and epidural) administration. The formulations may conveniently be presented in unit dosage form and may be prepared by any of the methods well known in the art of pharmacy. Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

For solid compositions, conventional non-toxic solid carriers include, for example, pharmaceutical grades of mannitol, lactose, cellulose, cellulose derivatives, starch, magnesium stearate, sodium saccharin, talcum, glucose, sucrose, magnesium carbonate, and the like may be used. The active compound as defined above may be formulated as suppositories using, for example, polyalkylene glycols, acetylated triglycerides and the like, as the carrier. Liquid pharmaceutically administrable compositions can, for example, be prepared by dissolving, dispersing, etc, an active compound as defined above and optional pharmaceutical adjuvants in a carrier, such as, for example, water, saline aqueous dextrose, glycerol, ethanol, and the like, to thereby form a solution or suspension. If desired, the pharmaceutical composition to be administered may also contain minor amounts of non-toxic auxiliary substances such as wetting or emulsifying agents, pH buffering agents and the like, for example, sodium acetate, sorbitan monolaurate, triethanolamine sodium acetate, sorbitan monolaurate, triethanolamine oleate, etc. Actual methods of preparing such dosage forms are known, or will be apparent, to those skilled in this art; for example, see Remington's Pharmaceutical Sciences, 20th edition, pub. Lippincott, Williams & Wilkins, 2000. The composition or formulation to be administered will, in any event, contain a quantity of the active compound(s) in an amount effective to alleviate the symptoms of the subject being treated.

Dosage forms or compositions containing active ingredient in the range of 0.25 to 95% with the balance made up from non-toxic carrier may be prepared.

For oral administration, a pharmaceutically acceptable non-toxic composition is formed by the incorporation of any of the normally employed excipients, such as, for example, pharmaceutical grades of mannitol, lactose, cellulose, cellulose derivatives, sodium crosscarmellose, starch, magnesium stearate, sodium saccharin, talcum, glucose, sucrose, magnesium carbonate, and the like. Such compositions take the form of solutions, suspensions, tablets, pills, capsules, powders, sustained release formulations and the like. Such compositions may contain 1%-95% active ingredient, more preferably 2-50%, most preferably 5-8%.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents and the like, such as for example, sodium acetate, sorbitan monolaurate, triethanolamine oleate, triethanolamine sodium acetate, etc.

The percentage of active compound contained in such parental compositions is highly dependent on the specific nature thereof, as well as the activity of the compound and the needs of the subject. However, percentages of active ingredient of 0.1% to 10% in solution are employable, and will be higher if the composition is a solid which will be subsequently diluted to the above percentages. Preferably, the composition will comprise 0.2-2% of the active agent in solution.

Ointments are typically prepared from the active compound and a paraffinic or a water-miscible ointment base.

Creams are typically prepared from the active compound and an oil-in-water cream base. If desired, the aqueous phase of the cream base may include, for example, at least about 30% w/w of a polyhydric alcohol, i.e., an alcohol having two or more hydroxyl groups such as propylene glycol, butane-1, 3-diol, mannitol, sorbitol, glycerol and polyethylene glycol and mixtures thereof. The topical formulations may desirably include a compound which enhances absorption or penetration of the active compound through the skin or other affected areas. Examples of such dermal penetration enhancers include dimethylsulfoxide and related analogues.

Formulations suitable for vaginal administration may be presented as pessaries, tampons, creams, gels, pastes, foams or spray formulations containing in addition to the active compound, such carriers as are known in the art to be appropriate.

General Synthesis Methods

Compounds of the present invention where $R^2$ is tetrazol-5-yl may be synthesised from compounds where $R^2$ is cyano, by treatment with sodium azide, trimethyltin azide or trimethylsilyl azide.

Compounds of the present invention where $R^2$ is carboxy may be synthesised from compounds where $R^2$ is an ester by a hydrolysis reaction, for example, using sodium hydroxide.

Compounds of formulae (I) to (IV), as well as their prescursors and protected forms, may be represented as:

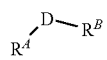

Formula 1 where $R^A$ represents $R^5$-L-A-, A' or precursors and protected forms thereof, and $R^B$ represents —(CH$_2$)$_n$—B, or precursors and protected forms thereof.

Compounds of Formula 1 where D is —C(=O)—N(R$^N$)—, may be synthesised by coupling compounds of Formula 2 and Formula 3, wherein the groups $R^A$ and $R^B$ are as defined above.

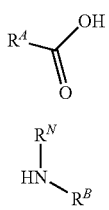

Formula 2

Formula 3

Such a coupling step may be carried out using a coupling agent or agents, for example, O-(7-azabenzotriazol-1-yl)-N,N,N',N'-tetramethyluronium hexafluorophosphate, TBTU and DIPEA, or EDC and HOAt.

Compounds of Formula 1, where D is —N(R$^N$)—C(=O)—, may be synthesised by coupling compounds of Formula 4 and Formula 5, wherein the groups $R^A$ and $R^B$ are as defined above.

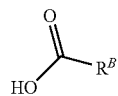

Formula 4

Formula 5

Such a coupling step may be carried out using a coupling agent or agents, as described above.

Compounds of Formula 1, where D is —CH$_2$—O— or —CH$_2$—S—, may be prepared by coupling compounds of Formulae 6 and 7, wherein the groups $R^A$ and $R^B$ are as defined above.

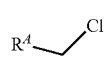

Formula 6

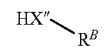

Formula 7 where X" is O or S, using NaH in an organic solvent, such as DMF and heptane or THF.

A key step in the synthesis of compounds of Formula 1, where D is —C(=O)—CH$_2$—, is the coupling of the remainder of the molecule to $R^A$. This can be achieved by coupling a compound of Formula 8:

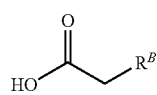

Formula 8 or precursor thereof to $R^A$ by a suitable method. For example, when A is:

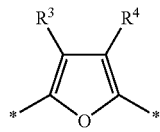

the coupling may take place in an organic solvent in the presence of P$_2$O$_5$.

Compounds of Formula 1 where D is —CHOH—CH$_2$— may be synthesized by reducing a compound of Formula 1 where D is —C(=O)—CH$_2$—, for example using sodium borohydride in an organic solvent.

Compounds of Formula 1 where D is —CH$_2$—CH$_2$— may be synthesized by dehydrating a compound of Formula 1 where D is —CH(OH)—CH$_2$—, for example using methansulphonyl chloride in an organic solvent.

Compounds of Formula 1, where D is —S—, may be prepared by coupling compounds of Formulae 9 and 10, wherein the groups $R^A$ and $R^B$ are as defined above.

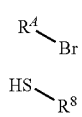

Formula 9

Formula 10 using K$_2$CO$_3$ in an organic solvent, such as acetone, with heating, for example in a microwave.

Compounds of Formula 1, where D is —C(=NH)—NH—, may be prepared by coupling compounds of Formula 11 and 12, wherein the groups R$^A$ and R$^B$ are as defined above.

Formula 11

Formula 12 by adding triethylaluminium solution to the compound of Formula 12 in an organic solvent, followed by addition of the compound of Formula 11, with heating.

Compounds of the present invention, where R$^5$ is an aryl group and L is a single bond, may be synthesised from compounds where R$^5$ is bromo by a Suzuki coupling of a compound of formula 13a (or equivalent ester of formula 13b):

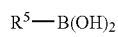

Formula 13a

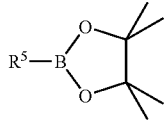

Formula 13b

The Suzuki coupling may be achieved using, for example, [1,1'-bis(diphenylphosphino)ferrocene]dichloropalladium (II) as the palladium catalyst. Alternatively, the coupling may be achieved using CsCO$_3$, with Pd(PPh$_3$)$_4$ as the palladium catalyst. In this reaction, other functional groups, for example, carboxy, should be appropriately protected.

Compounds of the present invention, where R$^5$ is an alkyl group and L is a single bond, and where A is:

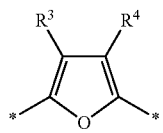

may be synthesized from compounds where A is:

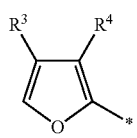

by reaction with R$^5$—Br, in the presence of AlCl$_3$, in an organic solvent, such as ortho-dichlorobenzene, followed by deprotection of the acid group. This method can be readily adapted for other A groups.

Compounds of formula V can be represented as Formula 14:

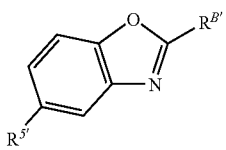

Formula 14 where R$^{B'}$ is B or a precursor thereof, and R$^{5'}$ is R$^5$-L- or a precursor thereof.

Compounds of Formula 14 can be synthesised by coupling compounds of Formulae 15 and 16:

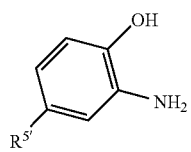

Formula 15

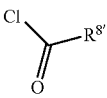

Formula 16 by reacting them together under appropriate conditions, for example with heating in NMP followed by basification with potassium carbonate.

Preferences

The following preferences may be combined with one another, and may be different for each aspect of the present invention.

R$^5$ may be a C$_{5-7}$ aryl group, such as furan-2-yl and phenyl.

R$^5$ is preferably a C$_6$ aryl group, and is more preferably phenyl. R$^5$ may be substituted, and preferred substituents include C$_{1-7}$ alkoxy groups, more preferably C$_{1-4}$ alkoxy groups, e.g. —OMe, —OCF$_3$, —OEt, —OCHF$_2$, with —OCHF$_2$ being the most preferred.

When R$^5$ is phenyl, preferable substituents include: C$_{1-4}$ alkyl (e.g. methyl, —CF$_3$, isopropyl); C$_{1-4}$ alkoxy (e.g. methoxy, —OCF$_3$), including substituted C$_{1-4}$ alkoxy (e.g. benzyloxy); C$_{5-6}$ aryl (e.g. phenyl); halo (e.g. Cl, F, di-Cl); acyl (e.g. —COMe); amino (e.g. —NH$_2$, —NMe$_2$); alkoxylene (e.g. —O—CH$_2$—O—). In some embodiments, C$_{1-4}$ alkyl (e.g. methyl, —CF$_3$, isopropyl); C$_{1-4}$ alkoxy (e.g. methoxy, —OCF$_3$); halo (e.g. Cl, F, di-Cl); acyl (e.g. —COMe); and alkoxylene (e.g. —O—CH$_2$—O—) are preferred.

The substituents may be any position of the phenyl ring, e.g. 2-, 3- and 4-, and when there are two substituents (e.g. di-chloro), these may be, for example, at: 2-, 3-; 2-, 4-; 3-, 5- or 3-, 4-.

R$^5$ may preferably be a C$_{9-10}$ aryl group, e.g. naphthyl (more preferably naphth-1-yl) and indolyl (more preferably indol-4-yl).

When R$^5$ is a C$_{4-20}$ alkyl group, it may be a C$_{4-10}$ alkyl group, and preferably a branched C$_{4-10}$ alkyl group, e.g. t-butyl, —CH$_2$—CH(CH$_3$)$_2$ or a cyclic alkyl group, such as cyclohexyl or adamantyl. Of these the cyclic groups are more preferred, with adamantyl being the most preferred.

In compounds of formulae (II), (III) and (V) L' is preferably a single bond.

In some embodiments, R$^4$ is selected from H, F, Cl, C$_{1-4}$ alkyl, C$_{1-4}$ alkoxy, C$_{5-7}$ aryl and C$_{5-7}$ aryl-C$_{1-4}$ alkyl groups.

In some embodiments, R$^3$ is selected from H, F, C$_{1-4}$ alkyl, C$_{1-4}$ alkoxy, C$_{5-7}$ aryl and C$_{5-7}$ aryl-C$_{1-4}$ alkyl groups.

When A is a five membered ring:

(i) $R^3$ (if present) is preferably selected from H and optionally substituted $C_{1-4}$ alkyl (in particular, methyl) and is most preferably H; and (ii) $R^4$ is preferably selected from H and optionally substituted $O_{1-4}$ alkyl (in particular, methyl) and is most preferably H.

When A is a six-membered ring, it is preferred that either:

(i) $R^3$, $R^4$ and $R^6$ (if present) are H; or (ii) one of $R^3$, $R^4$ and $R^6$ (if present) are Cl or F.

One preferred option when A is:

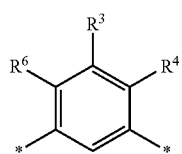

is for $R^4$ to be F.

A is preferably selected from:

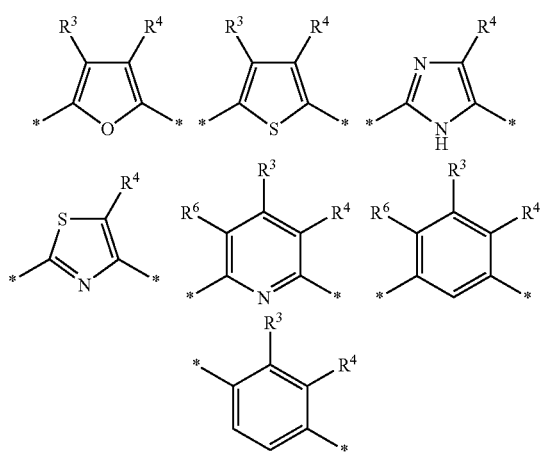

and is more preferably selected from:

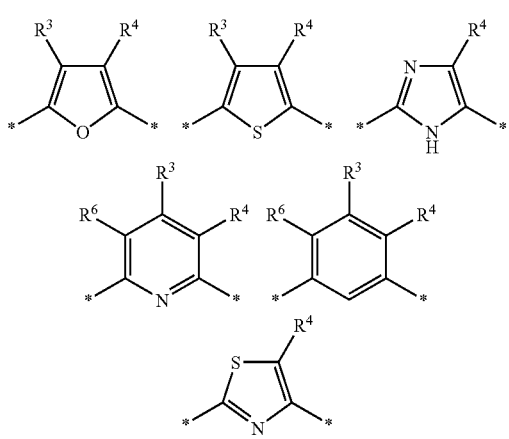

A is most preferably selected from:

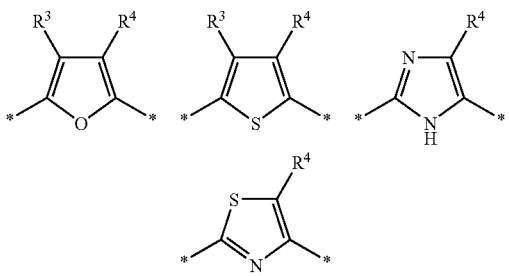

The most preferred option for A is:

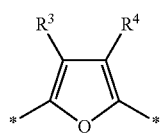

In compounds of formulae (III) to (V), D is preferably selected from:

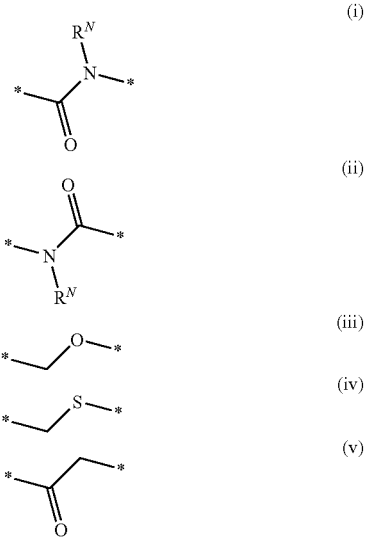

In compounds of formulae (I) and (III) to (V), D is more preferably selected from:

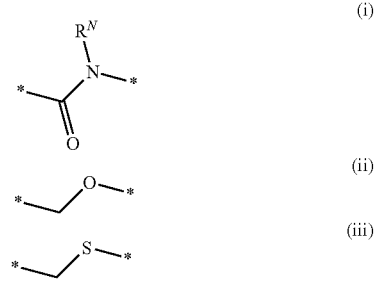

and is most preferably:

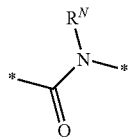

$R^N$ is preferably H or methyl, and is more preferably H.

In compounds of formula (II), D is preferably selected from:

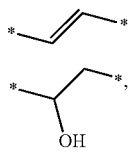

and in some embodiments D is:

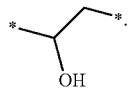

In compounds of formulae (IV) and (V), B is preferably selected from:

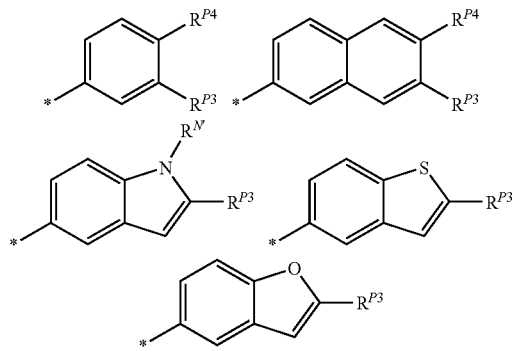

In compounds of formula (I), (II), (IV) and (V), B is more preferably selected from:

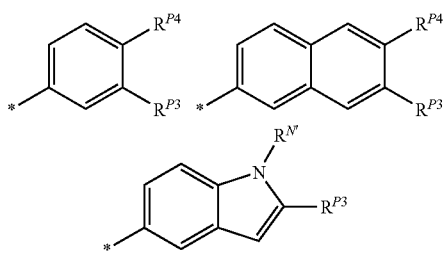

and most preferably:

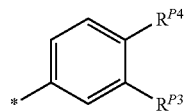

In compounds of formula (III), B is preferably:

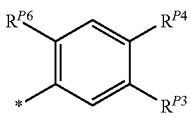

In compounds of formula (IV), T is preferably O. In some embodiments, A' is unsubstituted.

$R^2$ is preferably carboxy or tetrazoyl-5-yl, with carboxy being most preferred.

When $R^{P4}$ is H, $R^{P3}$ is preferably —CH=CH—$R^2$.

In some embodiments, m and n can only be 0 or 1, and m+n can only be 1 or 2. In these embodiments, preferably n+m=1, and more preferably n is 0 and m is 1.

In other embodiments, it is preferred that n is 0, and one of $R^{P3}$ and $R^{P4}$ (preferably $R^{P3}$) is —O—CH$_2$—$R^2$, wherein $R^2$ is preferably carboxy or tetrazol-5-yl, more preferably carboxy.

Particularly preferred compounds include:
3-{3-[(5-Phenoxy-furan-2-carbonyl)-amino]-phenyl}-acrylic acid (5);
3-{3-[(5-Benzoyl-furan-2-carbonyl)-amino]-phenyl}-acrylic acid (11);
3-[3-(6-Phenyl-pyridin-2-ylsulfanyl)-phenyl]-acrylic acid (16);
3-{3-[(Dibenzofuran-2-carbonyl)-amino]-phenyl}-acrylic acid (20);
3-{3-[2-Hydroxy-2-(5-phenyl-furan-2-yl)-ethyl]-phenyl}-acrylic acid (28);
3-{3-[2-(5-Phenyl-furan-2-yl)-vinyl]-phenyl}-acrylic acid (29);
3-{3-(5-Phenyl-benzoxazol-2-yl)-phenyl}-acrylic acid (34);
3-{6-[(5-Phenyl-furan-2-carbonyl)-amino]-pyridin-2-yl}-acrylic acid (40);
3-{4-Fluoro-3-[(5-phenyl-furan-2-carbonyl)-amino]-phenyl}-acrylic acid (45);
3-{4-Chloro-3-[(4-fluoro-biphenyl-3-carbonyl)-amino]-phenyl}-acrylic acid (52);
3-{3-[(4-Fluoro-biphenyl-3-carboximidoyl)-amino]-phenyl}-acrylic acid (58).

The selectivity of the compound for modulating EP$_2$ receptors over one or more of the other EP receptors (i.e. EP$_1$, EP$_3$, EP$_4$) can be quantified by dividing the Ki for EP$_2$ (see below) by the Ki for the other EP receptors (see below). The resulting ratio is preferably 10 or more, more preferably 100 or more.

SYNTHESIS EXAMPLES

Abbreviations

For convenience, many chemical moieties are represented using well known abbreviations, including but not limited to, methyl (Me), ethyl (Et), n-propyl (nPr), iso-propyl (iPr), n-butyl (nBu), sec-butyl (sBu), iso-butyl (iBu), tert-butyl (tBu), n-hexyl (nHex), cyclohexyl (cHex), phenyl (Ph), biphenyl (biPh), benzyl (Bn), naphthyl (naph), methoxy (MeO), ethoxy (EtO), benzoyl (Bz), and acetyl (Ac).

For convenience, the following abbreviations are used:

| | |
|---|---|
| d | doublet |
| DCM | dichloromethane |
| dd | doublet of doublets |
| DIPEA | N,N-diisopropylethylamine |
| DMAP | 4-(dimethylamino)-pyridine |
| DME | 1,2-dimethoxyethane |
| DMF | N,N-dimethylformamide |
| EDC | 1-(3-dimethylaminopropyl)-3-ethylcarbodiimide hydrochloride |
| eq | equivalent |
| EtOAc | ethyl acetate |
| EtOH | ethanol |
| HCl | hydrogen chloride |
| HOAt | 1-hydroxy-7-azabenzotriazole |
| $K_2CO_3$ | potassium carbonate |
| m | multiplet |
| MeCN | acetonitrile |
| MeOH | methanol |
| $MgSO_4$ | magnesium sulphate |
| NaOH | sodium hydroxide |
| $NaHCO_3$ | sodium bicarbonate |
| $Na_2SO_4$ | sodium sulphate |
| NMP | 1-methyl-2-pyrrolidinone |
| q | quartet |
| s | singlet |
| sept | septet |
| t | triplet |
| tlc | thin layer chromatography |
| TBME | tert-butyl methyl ether |
| TBTU | o-benzotriazol-1-yl-N,N,N',N'-tetramethyluronium tetrafluoroborate |
| THF | tetrahydrofuran |
| vol | volume |

General Methods

Commercially available reagents and solvents (HPLC grade) were used without further purification.

Microwave irradiation was carried out using a CEM Discover focused microwave reactor.

$^1$H NMR spectra were recorded on a Broker 400 MHz AV spectrometer in deuterated solvents. Chemical shifts (δ) are in parts per million and coupling constants are expressed in Hz. Thin-layer chromatography (TLC) analysis was performed with Kieselgel 60 $F_{254}$ (Merck) plates and visualized using UV light.

Analytical HPLC-MS was performed on Agilent HP1100, Waters 600 or Waters 1525 LC systems using reverse phase Hypersil BDS C18 columns (5 μm, 2.1×50 mm), gradient 0-95% B (A=water/0.1% TFA, B=acetonitrile/0.1% TFA) over 2.10 min, flow=1.0 ml/min. UV spectra were recorded at 215 nm using a Gilson G1315A Diode Array Detector, G1214A single wavelength UV detector, Waters 2487 dual wavelength UV detector, Waters 2488 dual wavelength UV detector, or Waters 2996 diode array UV detector. Mass spectra were obtained over the range m/z 150 to 850 at a sampling rate of 2 scans per second or 1 scan per 1.2 seconds using Micromass LCT with Z-spray interface or Micromass LCT with Z-spray or MUX interface. Data were integrated and reported using OpenLynx and OpenLynx Browser software.

Purification of compounds by preparative HPLC was performed on Gilson systems using reverse phase ThermoHypersil-Keystone Hyperprep HS C18 columns (12 μm, 100× 21.2 mm), gradient 20-100% B (A=water/0.1% TFA, B=acetonitrile/0.1% TFA) over 9.5 min, flow=30 ml/min, injection solvent 2:1 DMSO:acetonitrile (1.6 ml), UV detection at 215 nm.

Common Methods

A)

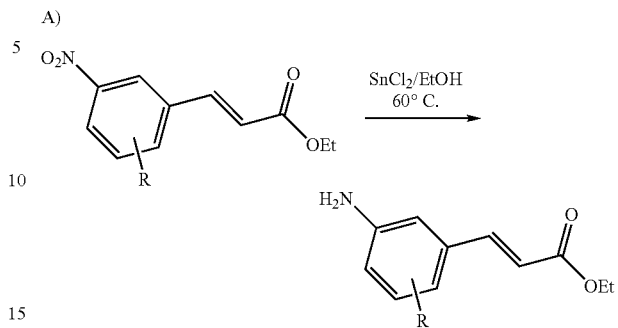

The nitro derivative was dissolved in EtOH (5 vol) and $SnCl_2.2H_2O$ (50 eq) was added as a solid. The resulting solution was then stirred at 60° C. for 2 hours. After cooling to ambient temperature, a pre-mixed solution of saturated Rochelle's salt (10 vol) and saturated $NaHCO_3$ solution (10 vol) was added to the reaction mixture and the aqueous layer was extracted with EtOAc (3×20 vol). The combined organic layers were dried ($MgSO_4$) and the solvent removed in vacuo.

B)

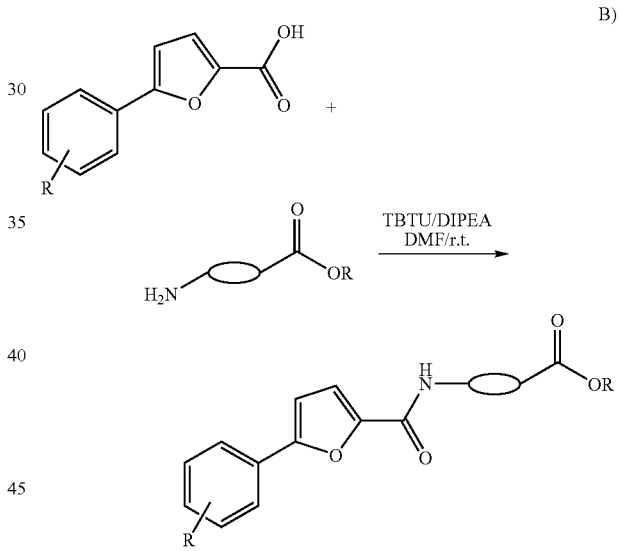

To a stirred solution of carboxylic acid (1 eq) and amino acid ester (1 eq) in DMF (20 vol) was added DIPEA (1 eq) followed by TBTU (1 eq). The reaction was stirred overnight, or until complete by LC/MS, at ambient temperature. To the reaction mixture was added EtOAc (30 vol) and the organic layer was washed with 2M HCl (2×50 vol), brine (2×50 vol), saturated aqueous $NaHCO_3$ (2×50 vol) and brine (2×50 vol). The organic layer was dried ($MgSO_4$), filtered and the solvent removed in vacuo.

C)

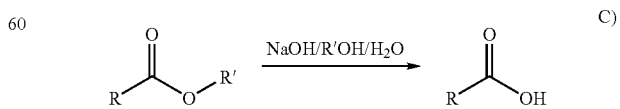

To a solution of ethyl ester in EtOH or MeOH (5 vol) was added 1M NaOH (5 vol) and the resulting solution was stirred for 30 min at ambient temperature. The EtOH was then removed in vacuo and the residue re-dissolved in TBME (50 vol) and water (50 vol). The aqueous layer was extracted with TBME (2×50 vol) then acidified with 2M HCl until a white precipitate formed. This was then extracted with EtOAc (3×50 vol). The organic layer was washed with brine, dried ($Na_2SO_4$), filtered and the solvent removed in vacuo

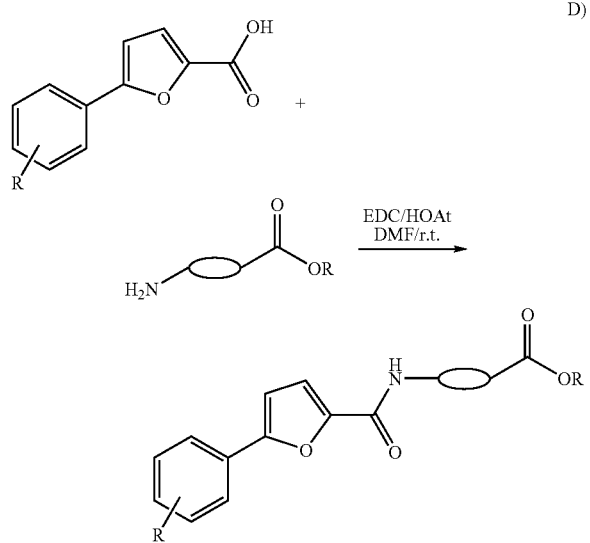

D)

The carboxylic acid (1 eq), EDC (1.2 eq), and HOAt (1.2 eq) were added to a vial as solids. The amino ester (1.2 eq) was dissolved in DMF (10 vol) and added to the vial. The reaction was stirred at ambient temperature overnight or until complete by LC/MS. Water (20 vol) was added and the mixture was extracted with EtOAc (3×10 vol). The organic layer was then washed with water (10 vol), dried ($MgSO_4$), filtered and concentrated in vacuo. Column chromatography using a stepped gradient of EtOAc in heptane gave the product.

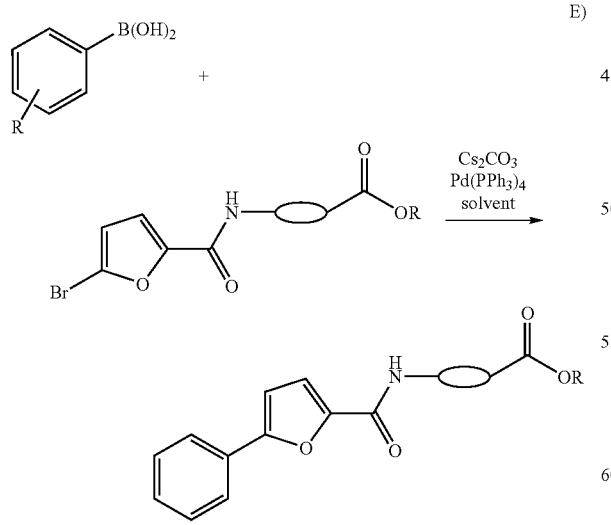

E)

To a suspension of the aryl bromide (1 eq), $Cs_2CO_3$ (1.2 eq) and boronic acid (1.1 eq) in toluene (15 vol) and MeOH (4 vol) was added $Pd(PPh_3)_4$ (0.1 eq). The resulting mixture was heated in a CEM Discover microwave for 30 min at 120° C. (150 W, 250 psi). Analysis was carried out by LC-MS and, if required, the reaction was heated again to drive the reaction to completion. Once complete, the reaction mixture was filtered through celite and the solvents removed in vacuo. The crude residue was re-dissolved in EtOAc and washed with water (3×5 vol). The combined organic layers were dried ($Na_2SO_4$), filtered and the solvents removed in vacuo. The compounds were then purified by column chromatography. If the ester group present was ethyl then EtOH was used instead of MeOH Work-up E1)

In some cases, LC-MS analysis showed that partial hydrolysis occurred during reaction.

In this case, after the solvents were removed in vacuo, the residue was re-dissolved in EtOAc (1.5 vol) and the organic layer was washed with 1M HCl (2×1 vol), dried ($Na_2SO_4$), filtered and the solvent removed in vacuo. The residue was triturated with TBME (1.5 vol).

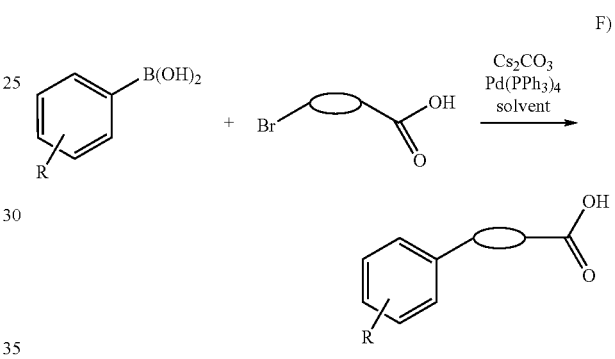

F)

To a suspension of the aryl bromide (1.2 eq), $Cs_2CO_3$ (4.0 eq) and boronic acid (1 eq) in toluene (5 vol) and EtOH (5 vol) under $N_2$ was added $Pd(PPh_3)_4$ (0.05 eq) and the resulting mixture was heated to 85° C. for 3 hours. The solvents were removed in vacuo and the solids re-suspended in EtOAc (10 vol). Water (10 vol) was then added and all the solids dissolved. The layers were separated and the aqueous layer was washed with EtOAc (3×5 vol) and acidified to pH 4 with 2M HCl upon which a precipitate formed. This was then extracted with EtOAc (2×10 vol). The combined organic layers were dried ($Na_2SO_4$) and removed in vacuo to give the product.

Example 1

3-{3-[(5-Phenoxy-furan-2-carbonyl)-amino]-phenyl}-acrylic acid (5)

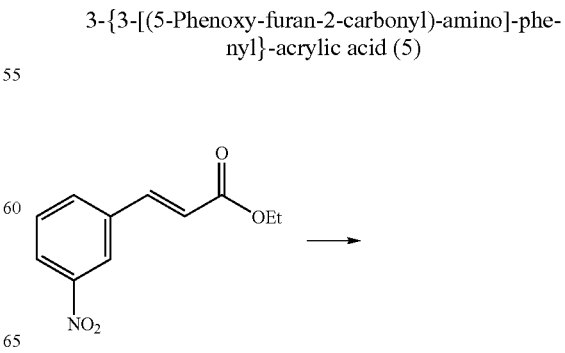

1

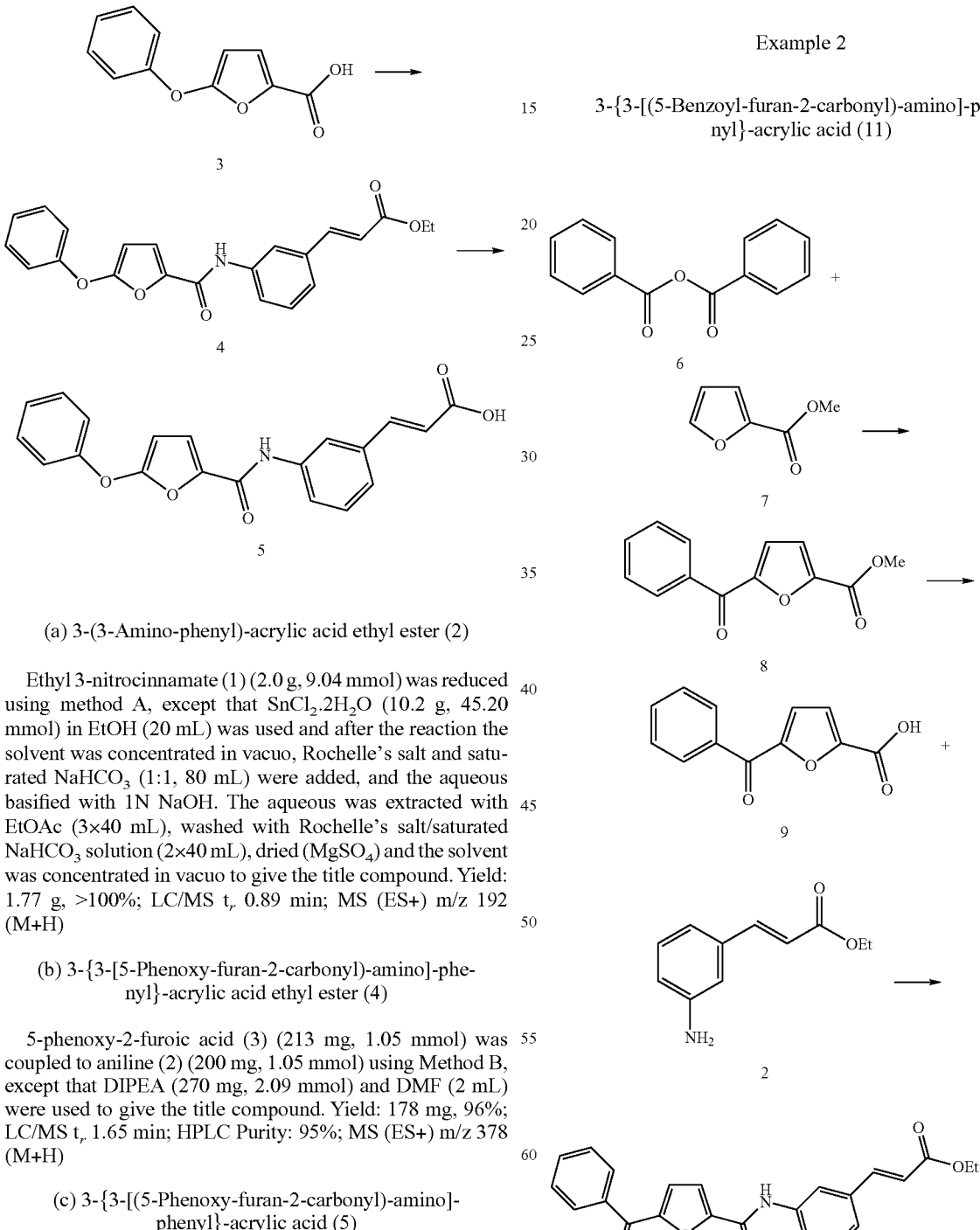

(a) 3-(3-Amino-phenyl)-acrylic acid ethyl ester (2)

Ethyl 3-nitrocinnamate (1) (2.0 g, 9.04 mmol) was reduced using method A, except that SnCl$_2$.2H$_2$O (10.2 g, 45.20 mmol) in EtOH (20 mL) was used and after the reaction the solvent was concentrated in vacuo, Rochelle's salt and saturated NaHCO$_3$ (1:1, 80 mL) were added, and the aqueous basified with 1N NaOH. The aqueous was extracted with EtOAc (3×40 mL), washed with Rochelle's salt/saturated NaHCO$_3$ solution (2×40 mL), dried (MgSO$_4$) and the solvent was concentrated in vacuo to give the title compound. Yield: 1.77 g, >100%; LC/MS t$_r$ 0.89 min; MS (ES+) m/z 192 (M+H)

(b) 3-{3-[5-Phenoxy-furan-2-carbonyl)-amino]-phenyl}-acrylic acid ethyl ester (4)

5-phenoxy-2-furoic acid (3) (213 mg, 1.05 mmol) was coupled to aniline (2) (200 mg, 1.05 mmol) using Method B, except that DIPEA (270 mg, 2.09 mmol) and DMF (2 mL) were used to give the title compound. Yield: 178 mg, 96%; LC/MS t$_r$ 1.65 min; HPLC Purity: 95%; MS (ES+) m/z 378 (M+H)

(c) 3-{3-[(5-Phenoxy-furan-2-carbonyl)-amino]-phenyl}-acrylic acid (5)

The ester (4) (100 mg, 0.27 mmol) was hydrolysed using method C, except that EtOH (1 mL), THF (0.5 mL) and 1M NaOH (1 mL) were used, and the reaction was stirred for 4 hours. The solvent was removed under a stream of nitrogen gas and the aqueous residue was acidified to pH 5 using 1N HCl, extracted with EtOAc (2×2 mL), dried (MgSO$_4$), filtered and the solvent concentrated in vacuo to give the title compound as an off-white solid. Yield: 89 mg, 96%; LC-MS t$_r$ 1.47 min; HPLC Purity: 100%; MS (ES+) m/z 350 (M+H)

$^1$H NMR (400 MHz; DMSO): δ 5.95 (d, 1H), 6.45 (d, 1H) 7.20-7.30 (m, 3H), 7.35-7.60 (m, 6H), 7.80 (d, 1H), 8.00 (s, 1H), 10.15 (s, 1H), 12.50 (br. s, 1H)

Example 2

3-{3-[(5-Benzoyl-furan-2-carbonyl)-amino]-phenyl}-acrylic acid (11)

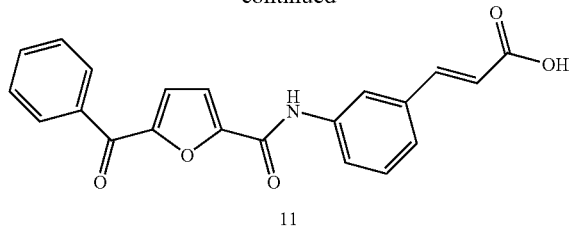

11

(a) 5-Benzoyl-furan-2-carboxylic acid methyl ester (8)

Methyl 2-furoate (7) (100 mg, 0.79 mmol), Iron(III) chloride (193 mg, 1.19 mmol) and benzoic anhydride (6) (180 mg, 0.79 mmol) were combined and stirred in DCM at ambient temperature overnight. The reaction mixture was filtered and the organic layer was washed with saturated $NaHCO_3$ solution, dried ($MgSO_4$), filtered and the solvent concentrated in vacuo. The crude product was partially purified using column chromatography eluting with 10-20% EtOAc in heptane. Excess benzoic acid was removed by dissolving the product in DCM and washing with saturated $NaHCO_3$ solution (×3). The organic layer was dried ($MgSO_4$), filtered and the solvent concentrated in vacuo to give the title compound. Yield: crude 80 mg, 44%; LC $t_r$ 1.29 min

(b) 5-Benzoyl-furan-2-carboxylic acid (9)

The crude ester (8) (80 mg, 0.35 mmol) was hydrolysed using Method C, except that MeOH (0.8 mL) and 1 M NaOH (0.8 mL) were used. After the reaction, the solvent was removed under a stream of nitrogen gas, acidified using 1N HCl, extracted with EtOAc, dried ($MgSO_4$), filtered and the solvent concentrated in vacuo to give the crude title compound. Yield: 48 mg; HPLC Purity: >66%; LC $t_r$ 0.09 min

(c) 3-{3-[(5-Benzoyl-furan-2-carbonyl)-amino]-phenyl}-acrylic acid ethyl ester (10)

Acid (9) (48 mg, 0.22 mmol) was coupled to aniline (2) (43 mg, 0.22 mmol) using Method B, except that DIPEA (57 mg, 0.44 mmol) and DMF (0.5 mL) were used. The crude product was purified by preparative HPLC to give the title compound. Yield: 28 mg; LC-MS $t_r$ 41.54 min; MS (ES+) m/z 389 (M+H)

(d) 3-{3-[(5-Benzoyl-furan-2-carbonyl)-amino]-phenyl}-acrylic acid (11)

The ester (10) (28 mg, 0.072 mmol) was hydrolysed using Method C, except that EtOH (0.15 mL) and 1M NaOH (0.15 mL) were used. After the reaction, the solvent was removed under a stream of nitrogen gas and the residue acidified to pH 5 using 1N HCl. The precipitate was filtered off and dried to give the title compound. Yield: 8 mg, 31%; LC-MS $t_r$ 1.95 min; HPLC Purity: 98%; MS (ES+) m/z 362 (M+H); $^1$H NMR (400 MHz; DMSO): δ 6.4 (d, 1H), 7.10 (d, 1H), 7.20- 7.40 (m, 2H), 7.55 (m, 1H), 7.60-7.80 (m, 3H), 7.80-7.90 (d, 1H), 7.95 (s, 1H), 7.95-8.10 (m, 3H)

Example 3

3-[3-(6-Phenyl-pyridin-2-ylsulfanyl)-phenyl]-acrylic acid (16)

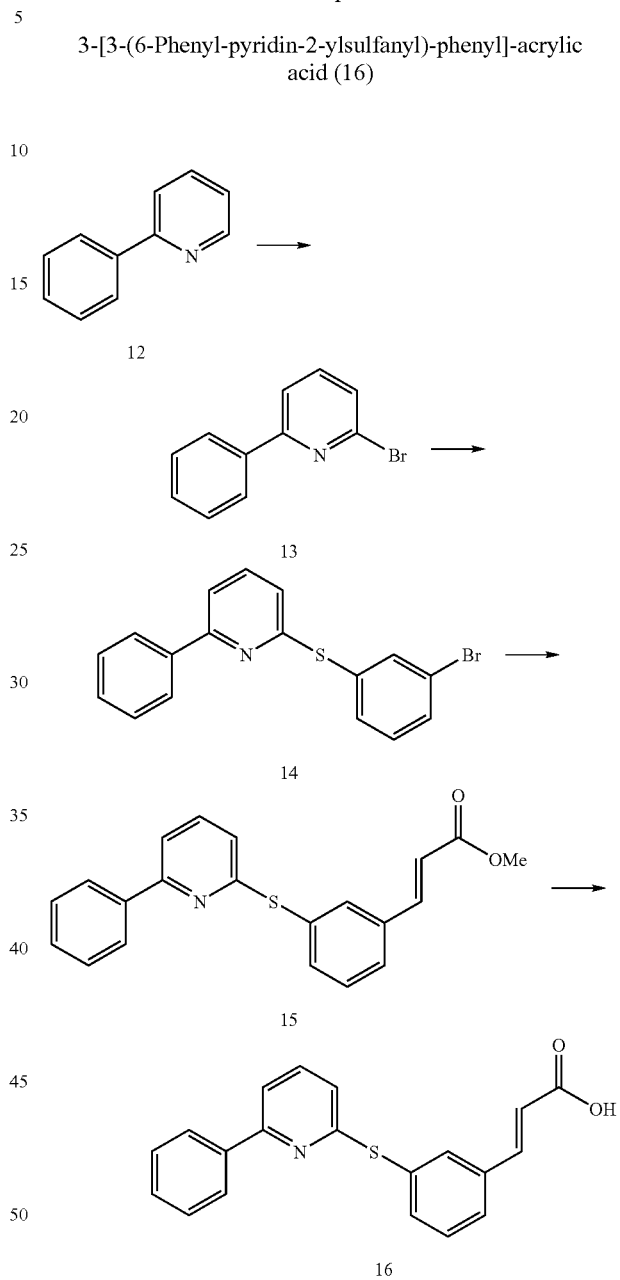

(a) 2-Bromo-6-phenyl-pyridine (13)

To N,N-dimethylethanolamine (0.8 mL, 8.00 mmol) in heptane (10 mL) cooled externally to 0° C. was added dropwise a 2.5 M n-butyllithium solution (6.40 mL) and the reaction mixture stirred for 30 minutes. 2-Phenylpyridine (12) (412 mg, 2.66 mmol) in heptane (5 mL) was then added and the reaction mixture stirred for a further 1 hour. The reaction was then cooled and carbon tetrabromide (3.18 g, 9.60 mmol) was added whilst maintaining the temperature at −78° C. The reaction was kept at −78° C. for 1 hour and then allowed to warm to ambient temperature. Water was cautiously added and extracted with TBME (×2), dried (Na$_2$SO$_4$) and the solvent concentrated in vacuo. The crude product was purified by column chromatography eluting with 5% EtOAc in heptane to give the title compound. Yield: 300 mg, 48%; LC-MS t$_r$ 1.63 min; HPLC Purity: 97%; MS (ES+) m/z 234, 236 (M+H)

(b) 2-(3-Bromo-phenylsulfanyl)-6-phenyl-pyridine (14)

2-Bromo-6-phenyl-pyridine (13) (100 mg, 0.43 mmol), K$_2$CO$_3$ (117 mg, 0.85 mmol) in acetone (2 mL) was added 3-bromothiophenol and the reaction mixture was heated in a CEM Discover microwave for 1×30 minutes at 90° C., then 4×2 hours at 130° C., followed by 1×8 hours at 130° C. The crude product was partially purified by column chromatography eluting with 10% EtOAc in heptane to give the title compound. Yield: 100 mg, 68%; LC-MS t$_r$ 1.97 min; HPLC Purity: 55%; MS (ES+) m/z 342, 344 (M+H)

(c) 3-[3-(6-Phenyl-pyridin-2-ylsulfanyl)-phenyl]-acrylic acid methyl ester (15)

Crude aryl bromide (14) (100 mg, 0.18 mmol), methyl acrylate (18 mg, 0.21 mmol), triethylamine (71 mg, 0.70 mmol), tri(o-toly)phosphine (5 mg, 0.016 mmol) and palladium(II) acetate (12 mg, 0.054 mmol) in acetonitrile (2 mL) was heated in a CEM Discover microwave for 45 minutes at 90° C. More tri(o-toly)phosphine (3 mg) and palladium(II) acetate (3 mg) were added and the reaction mixture retreated in the microwave for 20 minutes; palladium(II) acetate (2 mg) was then added and the process repeated for a further 25 minutes. The solvent was removed under a stream of nitrogen gas, water was added, and the organics extracted with EtOAc, washed with water, dried (Na$_2$SO$_4$) and the solvent concentrated in vacuo. The crude product was partially purified by column chromatography. Yield: 51 mg, 60%; LC-MS t$_r$ 1.82 min; HPLC Purity: 70%; MS (ES+) m/z 348 (M+H)

(d) 3-{3-(6-Phenyl-pyridin-2-ylsulfanyl)-phenyl}-acrylic acid (16)

The ester (15) (51 mg, 0.11 mmol) was hydrolysed using Method C, except that the reaction was stirred for 2 hours. The crude solid was purified by preparative HPLC to provide the title compound. Yield: 3 mg, 10%; LC-MS t$_r$ 1.65 min; HPLC Purity: 100%; MS (ES+) m/z 334 (M+H); $^1$H NMR (400 MHz; MeOH): δ 6.65 (d, 1H), 7.05 (d, 1H), 7.45-7.55 (m, 3H), 7.60-7.65 (dd, 1H), 7.65-7.85 (m, 5H), 8.00 (m, 3H)

Example 4

3-{3-[(Dibenzofuran-2-carbonyl)-amino]-phenyl}-acrylic acid (20)

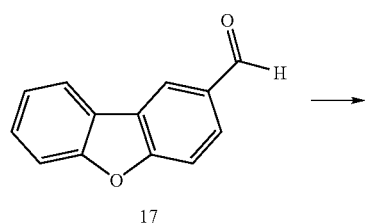

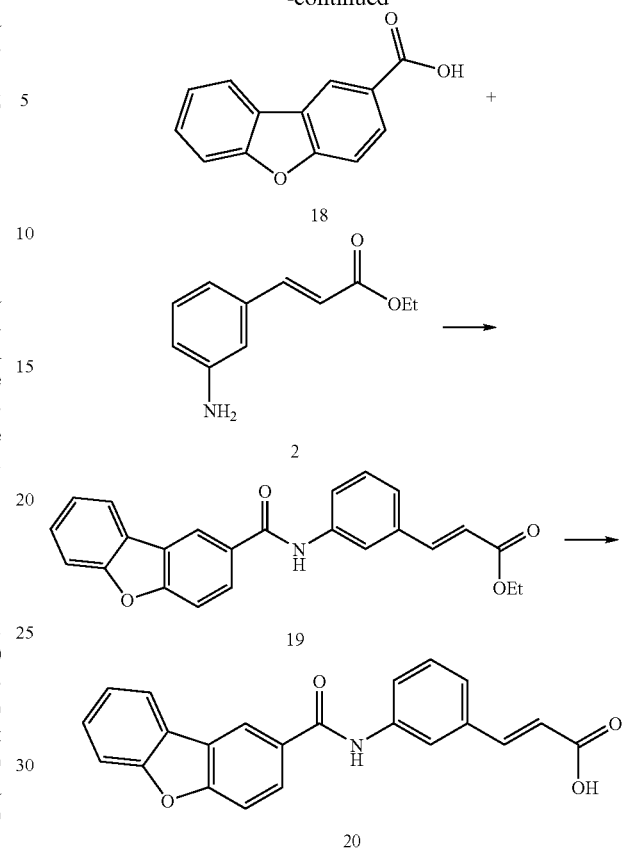

(a) Dibenzofuran-2-carboxylic acid (18)

To dibenzofuran-2-carboxaldehyde (17) (200 mg, 1.02 mmol) was added solid NaOH (49 mg, 1.22 mmol) then 10% NaOH solution (1.8 mL). Silver nitrate (173 mg, 1.02 mmol) was then added, the reaction mixture heated to 60° C. for 1.5 hours and then stirred overnight at ambient temperature. The reaction mixture was then filtered and washed with water. The filtrate was acidified to pH 2 using concentrated HCl and the precipitated product filtered and dried to give the title compound as an off-white solid. Yield: 83 mg, 38%; LC-MS t$_r$ 1.31 min; HPLC Purity: 100%; MS (ES+) m/z not detectable (M+H)

(b) 3-{3-[(Dibenzofuran-2-carbonyl)-amino]-phenyl}-acrylic acid ethyl ester (19)

Acid (18) (50 mg, 0.24 mmol) was coupled to aniline (2) (54 mg, 0.28 mmol) using Method D, except that DMF (1 mL) was used. The product was further purified by trituration in DCM/heptane to give the title compound. Yield: 46 mg, 51%; LC-MS t$_r$ 1.70 min; HPLC Purity: 97-100%; MS (ES+) m/z 386 (M+H)

(c) 3-{3-[(Dibenzofuran-2-carbonyl)-amino]phenyl}-acrylic acid (20)

The ester (19) (46 mg, 0.12 mmol) was hydrolysed using Method C, except that MeOH (1 mL) and THF (1 mL) were used, and the reaction mixture was heated to 40° C. for 1 hour. After the reaction, TBME was added and the mixture acidified using 6N HCl. The aqueous was extracted with more TBME (×3), EtOAc (×3), dried (MgSO$_4$) and the solvent concentrated in vacuo. The crude solid was triturated with DCM, filtered, washed with heptane and dried to give the title compound. Yield: 34 mg, 81%; LC-MS t$_r$ 2.08 min; HPLC Purity: 100%; MS (ES+) m/z 358 (M+H); $^1$H NMR (400 MHz; DMSO): δ 6.60 (d, 1H), 7.55-7.75 (m, 5H), 7.9 (d, 1H), 7.95-8.05 (m, 2H), 8.25 (s, 1H), 8.30 (d, 1H), 8.40 (d, 1H), 8.95 (s, 1H), 10.65 (s, 1H)

Example 5

3-{3-[2-Hydroxy-2-(5-phenyl-furan-2-yl)-ethyl]-phenyl}-acrylic acid (28)

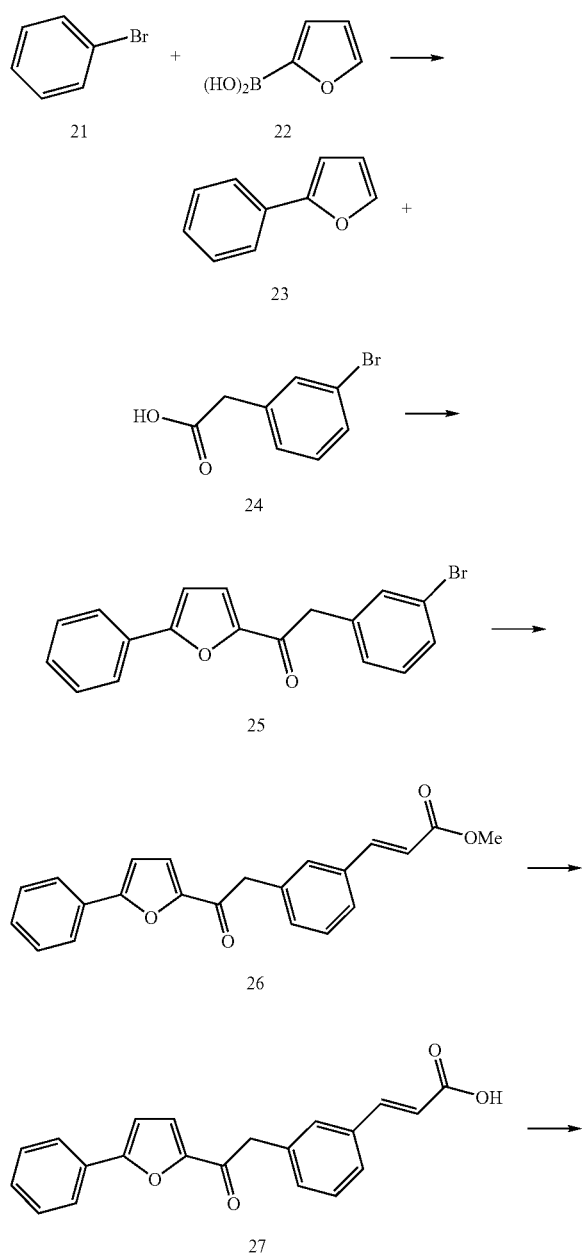

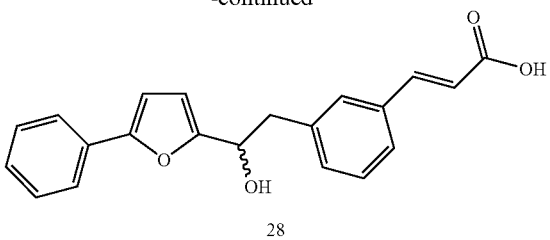

(a) 2-Phenyl-furan (23)

Furan-2-boronic acid (22) (3.6 g, 32.14 mmol) was coupled to bromobenzene (21) (4.2 g, 26.79 mmol) using Method E, except that Cs$_2$CO$_3$ (17.47 g, 53.58 mmol), Pd(P-Ph$_a$)$_4$ (6.20 g, 0.54 mmol), toluene (25 mL) and EtOH (25 mL) were used and the reaction heated in a CEM Discover microwave at 140° C. (200 W, 200 psi). The crude product was purified by dry-flash chromatography eluting with EtOAc in heptane to yield the title compound. Yield: 2.94 g, 62%; LC t$_r$ 1.50 min; HPLC Purity: 84%

(b) 2-(3-Bromo-phenyl)-1-(5-phenyl-furan-2-yl)-ethanone (25)

Phosphorous pentoxide (2.02 g, 14.20 mmol) suspended in 1,2-dichlorobenzene (60 mL) was added to a mixture of 2-phenyl-furan (23) (500 mg, 2.84 mmol) and 3-bromophenylacetic acid (24) (1.34 g, 6.25 mmol). The reaction mixture was heated to 80° C. for 2 hours and then cooled to ambient temperature. DCM was added, the organic layer washed with water and partially reduced in vacuo. The crude product was purified by Flash Master Jones Chromatography using a 50 g silica cartridge and first eluting with heptane to remove excess 1,2-dichlorobenzene, then 5-10% EtOAc in heptane to give the title compound. Yield: 278 mg, 38%; LC-MS t$_r$ 1.73 min; HPLC Purity: 100%; MS (ES+) m/z 341, 343 (M+H)

(c) 3-{3-[2-Oxo-2-(5-phenyl-furan-2-yl)-ethyl]-phenyl}-acrylic acid methyl ester (26)

Tri(o-tolyl)phosphine (25 mg, 0.082 mmol) and palladium (II) acetate (9 mg, 0.041 mmol) in acetonitrile (1 mL) was added to a mixture of methyl acrylate (84 mg, 0.98 mmol) and triethylamine (329 mg, 3.26 mmol). Aryl bromide (25) (278 mg, 0.82 mmol) in acetonitrile (3 mL) was then added and the reaction mixture heated in a CEM Discover microwave for 45 minutes at 90° C. The solvent was concentrated in vacuo, and the crude product was purified by Flash Master Jones Chromatography using a 25 g silica cartridge eluting with 5-17% EtOAc in heptane. Yield: 222 mg, 78%; LC-MS t$_r$ 1.62 min; HPLC Purity: 100%; MS (ES+) m/z 347 (M+H)

(d) 3-(3-[2-Oxo-2-(5-phenyl-furan-2-yl)-ethyl]-phenyl)-acrylic acid (27)

The ester (26) (222 mg, 0.64 mmol) was hydrolysed using Method C, except that MeOH (1 mL), THF (1 mL) and 1 M NaOH (1 mL) were used, and the reaction was stirred for 1.5 hours. After work-up, the crude product was triturated with DCM/heptane (×3) to provide the title compound. Yield: 134 mg; LC t$_r$ 1.39 min; HPLC Purity: 92%

(e) 3-{3-[2-Hydroxy-2-(5-phenyl-furan-2-yl)-ethyl]-phenyl}-acrylic acid (28)

To ketone (27) (33 mg; 0.10 mmol) dissolved in MeOH (2 mL) was added sodium borohydride (8 mg, 0.21 mmol). Subsequent additions of sodium borohydride (2 mg) were added until the reaction was complete. The reaction mixture was acidified to pH 5 by dropwise addition of 1N HCl and extracted with TBME (×3). The organic layer was dried ($MgSO_4$) and the solvent concentrated in vacuo to give the title compound as a white solid. Yield: 20 mg, 61%; LC-MS $t_r$ 2.02 min; HPLC Purity: 100%; MS (ES+) m/z 335 (M+H), 317 (M−$H_2O$+H); $^1$H NMR (400 MHz; $CDCl_3$): δ 3.20-3.30 (d, 2H), 5.0 (t, 1H), 6.3 (d, 1H), 6.40 (d, 1H), 6.60 (d, 1H), 7.20-7.50 (m, 7H), 7.65-7.80 (m, 3H)

Example 6

3-{3-[2-(5-Phenyl-furan-2-yl)-vinyl]-phenyl}-acrylic acid (29)

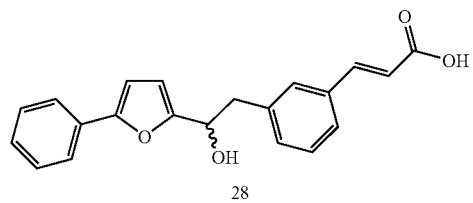

28

29

To acid (28) (9.2 mg, 0.028 mmol) in DCM (1 mL), externally cooled to −78° C., was added methanesulphonyl chloride, (20 mg, 0.17 mmol) and triethylamine (29 mg, 0.29 mmol). The solution was then allowed to warm to ambient temperature and stirred for a further 2 hours. The solvent was concentrated in vacuo and the residue purified by Flash Master Jones Chromatography using a 2 g silica cartridge and eluting with 50% EtOAc in heptane to give the title compound as a white solid. Yield: 3.6 mg, 41%; LC-MS $t_r$ 1.77 min; NMR Purity: >85%; MS (ES+) m/z 317 (M+H); $^1$H NMR (400 MHz; DMSO): δ 6.70-6.80 (m, 2H), 7.15 (d, 1H), 7.25-7.35 (d, 1H), 7.35-7.45 (m, 2H), 7.50-7.60 (m, 4H), 7.65-7.75 (m, 3H), 7.90 (d, 2H), 8.10 (s, 1H)

Example 7

3-[3-(5-Phenyl-benzoxazol-2-yl)-phenyl]-acrylic acid (34)

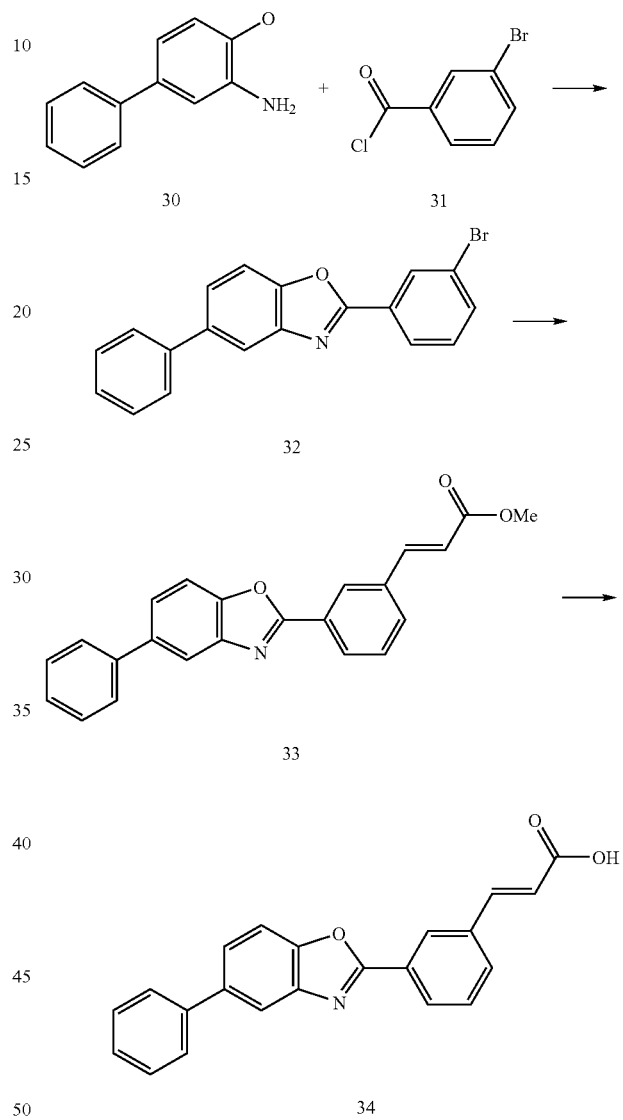

(a) 2-(3-Bromo-phenyl)-5-phenyl-benzoxazole (32)

2-amino-4-phenylphenol (30) (250 mg, 1.20 mmol) and 3-bromo-benzoyl chloride (31) (265 mg, 1.20 mmol) were heated in NMP at 150° C. overnight. The reaction was cooled to ambient temperature then $K_2CO_3$ (aq) and brine were added, and the aqueous extracted with EtOAc (×5). The organic layer was washed with brine, dried ($Na_2SO_4$), and the solvent concentrated in vacuo. The crude product was purified by column chromatography eluting with a mixture of 1:1 DCM in heptane to yield the title compound. Yield: 210 mg, 49%; LC-MS $t_r$ 2.02 min; HPLC Purity: 67%; MS (ES+) m/z 350, 352 (M+H)

(b) 3-[3-(5-Phenyl-benzoxazol-2-yl)-phenyl]-acrylic acid methyl ester (33)

Tri(o-tolyl)phosphine (9 mg, 0.030 mmol), palladium(II) acetate (6 mg, 0.027 mmol), methyl acrylate (31 mg, 0.34 mmol), triethylamine (116 mg, 1.14 mmol) and aryl bromide (32) (100 mg, 0.29 mmol) in acetonitrile (3 mL) were heated in a CEM Discover microwave for 90 minutes at 90° C. The solvent was removed under a stream of nitrogen gas, water was added and the organics extracted with EtOAc. The organic layer was dried ($Na_2SO_4$) and the solvent concentrated in vacuo. The crude product was purified by column chromatography eluting with 20% EtOAc in heptane. Yield: 41 mg, 40%; LC-MS $t_r$ 1.86 min; HPLC Purity: 67%; MS (ES+) m/z 356 (M+H)

(c) 3-[3-(5-Phenyl-benzoxazol-2-yl)-phenyl]-acrylic acid (34)

The ester (33) (41 mg, 0.12 mmol) was hydrolysed using Method C, except that MeOH (3 mL), THF (3 mL) and 1M NaOH (5 mL) were used, and the reaction was stirred for 2 hours. Yield: 21 mg, 53%; LC-MS $t_r$ 1.74 min; HPLC Purity: 96%; MS (ES+) m/z 342 (M+H); $^1$H NMR (400 MHz; DMSO): δ 6.7 (d, 1H), 7.4 (t, 1H), 7.45-7.55 (t, 2H), 7.70-7.80 (m, 5H), 7.9 (d, 1H), 8.05 (d, 1H), 8.10 (s, 1H), 8.30 (d, 1H), 8.50 (s, 1H), 12.55 (br. s, 1H)

Example 8

3-{6-[(5-Phenyl-furan-2-carbonyl)-amino]-pyridin-2-yl}-acrylic acid (40)

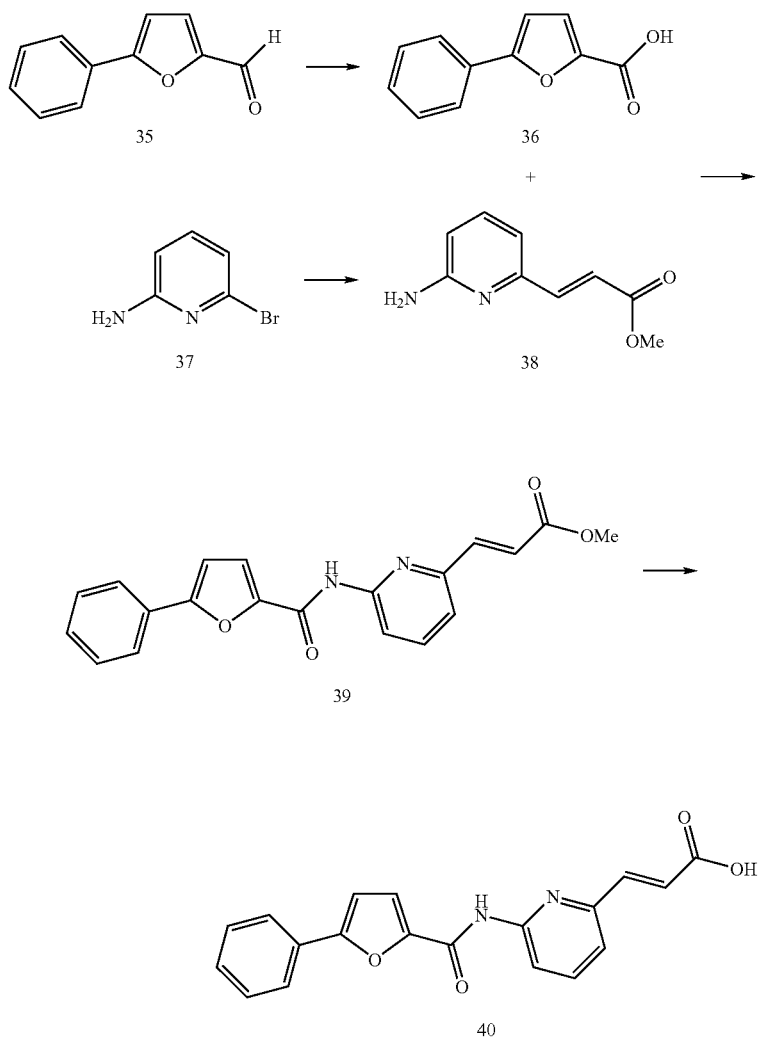

(a) 5-Phenyl-furan-2-carboxylic acid (36)

To 5-phenyl-2-furaldehyde (35) (690 mg, 4.01 mmol) was added solid NaOH (176 mg, 4.40 mmol) then 10% NaOH solution (6.2 mL). Silver nitrate (680 mg, 4.00 mmol) was added and the reaction mixture heated to 60° C. for 4.5 hours then cooled to ambient temperature. The reaction mixture was then filtered and washed with water. The filtrate was acidified to pH 2 using 2N HCl and the precipitated product filtered and dried to give the title compound.

Yield: 527 mg, 70%; LC-MS $t_r$ 1.57 min; HPLC Purity: 98%; MS (ES+) m/z 189 (M+H)

(b) 3-(6-Amino-pyridin-2-yl)-acrylic acid methyl ester (38)

Tri(o-toly)phosphine (26 mg, 0.086 mmol), palladium(II) acetate (214 mg, 0.96 mmol), methyl acrylate (90 mg, 1.04 mmol), triethylamine (351 mg, 3.47 mmol) and 2-amino-6-bromopyridine (37) (150 mg, 0.87 mmol) in acetonitrile (3 mL) were heated in a CEM Discover microwave for 1 hour at 90° C. The solvent was removed under a stream of nitrogen gas; 4N HCl was added and the aqueous extracted with TBME (×2). The aqueous layer was then basified to pH 9/10 using $K_2CO_3$(aq) and extracted with EtOAc (×5). The organic layer was washed with brine, dried ($Na_2SO_4$) and the solvent concentrated in vacuo. The crude product was partially purified by column chromatography eluting with 50% EtOAc in heptane to give the title compound. Yield: 95 mg, 61%; LC-MS $t_r$ 0.76 min; HPLC Purity: 42%; MS (ES+) m/z 179 (M+H)

(c) 3-{6-[(5-Phenyl-furan-2-carbonyl)-amino]-pyridin-2-yl}-acrylic acid methyl ester (39)

To acid (36) (100 mg, 0.53 mmol) was added thionyl chloride (0.5 mL), a catalytic amount of DMF (1 drop) and the reaction heated at 50° C. for 30 minutes. After cooling the solvent was concentrated in vacuo and azeotroped with toluene to provide the in situ acid chloride. To the acid chloride was added amine (38) (95 mg, 0.53 mmol) and DIPEA (69 mg, 0.53 mmol) in DCM (2 mL), and the reaction mixture stirred at ambient temperature overnight. $K_2CO_3$ (aq) was then added and the aqueous layer extracted with DCM. The organic layer was washed with water, dried ($Na_2SO_4$) and the solvent concentrated in vacuo. The residue was partially purified using column chromatography eluting with 50% EtOAc in heptane to give the title compound. Yield: 35 mg, 19%; LC-MS $t_r$ 1.67 min; HPLC Purity: 52%; MS (ES+) m/z 349 (M+H)

(d) 3-{6-[(5-Phenyl-furan-2-carbonyl)-amino]-pyridin-2-yl}-acrylic acid (40)

The ester (39) (35 mg, 0.10 mmol) was hydrolysed using Method C, except that EtOH (2 mL), THF (1 mL) and 1 M NaOH (2 mL) were used, and the reaction was stirred for 2 hours. After work-up, the crude product was purified by preparative HPLC to give the title compound. Yield: 9.8 mg, 29%; LC-MS $t_r$ 2.00 min; HPLC Purity: 97%; MS (ES+) m/z 335 (M+H); $^1$H NMR (400 MHz; MeOH): δ 6.95 (d, 1H), 7.05 (d, 1H), 7.35-7.55 (m, 5H), 7.65 (d, 1H), 7.85-8.00 (m, 3H), 8.30 (d, 1H)

Example 9

3-{4-Fluoro-3-[(5-phenyl-furan-2-carbonyl)-amino]-phenyl}-acrylic acid (45)

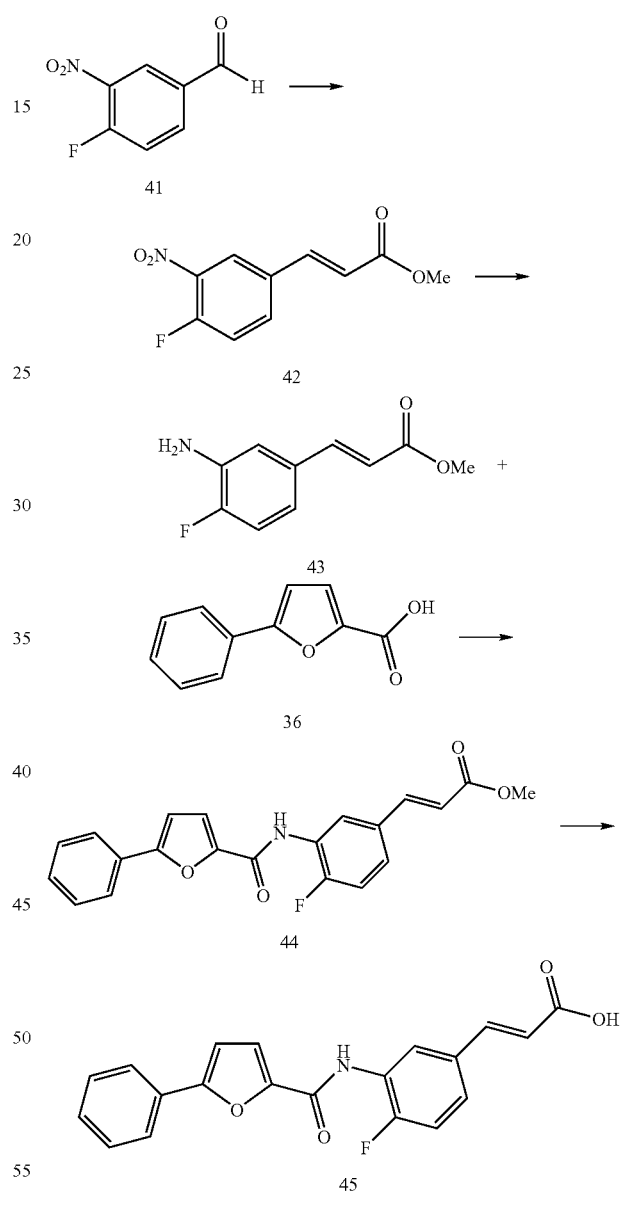

(a) 3-(4-Fluoro-3-nitro-phenyl)-acrylic acid methyl ester (42)

Trimethyl phosphonoacetate (182 mg, 1.00 mmol) in THF (1.70 mL) was added dropwise (caution—vigorous reaction!) to sodium hydride (60% in oil) (60 mg, 1.50 mmol) in THF (1.70 mL) under an atmosphere of nitrogen at 0° C. The reaction mixture was stirred for 15 minutes at 0° C. and then 4-fluoro-3-nitrobenzaldehyde (169 mg, 1.00 mmol) in THF (0.50 mL) was added. After 1 hour, EtOAc/water was added and the organic layer washed with more water, dried (Na$_2$SO$_4$), and the solvent concentrated in vacuo. The crude product was purified by column chromatography eluting with 33% EtOAc in heptane to give the title compound. Yield: 160 mg, 71%; LC-MS 41.31 min; HPLC Purity: >75%; MS (ES+) m/z not detectable (M+H)

(b) 3-(3-Amino-4-fluoro-phenyl)-acrylic acid methyl ester (43)

The crude nitro compound (42) (160 mg, 0.71 mmol) was reduced using Method A, except that SnCl$_2$.2H$_2$O (0.80 g, 3.55 mmol) and EtOH (3.2 mL) were used. The crude product was purified by column chromatography eluting with 25% EtOAc in heptane to give the title compound. Yield: 65 mg, 47%; LC-MS $t_r$ 1.14 min; HPLC Purity: 88%; MS (ES+) m/z 195 (M+H)

(c) 3-{4-Fluoro-3-[(5-phenyl-furan-2-carbonyl)-amino]-phenyl}-acrylic acid methyl ester (44)

5-phenyl-2-furoic acid (36) (18 mg, 0.15 mmol) was coupled to aniline (43) (30 mg, 0.15 mmol) using Method B, except that DIPEA (40 mg, 0.31 mmol) and DMF (2 mL) were used and the reaction was stirred at ambient temperature for 2.5 hours, then at 40° C. for 24 hours. Further TBTU (1 eq) and acid (1 eq) were added and the reaction heated at 60° C. for a further 6 hours to give the crude title compound after work-up. The residue was purified using column chromatography eluting with 20% EtOAc in heptane to give the title compound. Yield: 18 mg, 32%; LC-MS $t_r$ 1.55 min; HPLC Purity: 83%; MS (ES+) m/z 366 (M+H)

(d) 3-{4-Fluoro-3-[(5-phenyl-furan-2-carbonyl)-amino]-phenyl}-acrylic acid (45)

The ester (44) (18 mg, 0.049 mmol) was hydrolysed using Method C, except that MeOH (1 mL), THF (1 mL) and 1M NaOH (2 mL) were used, and the reaction was stirred for 1 hour. Yield: 3 mg, 17%; LC-MS $t_r$ 1.44 min; HPLC Purity: 91%; MS (ES+) m/z 352 (M+H); $^1$H NMR (400 MHz; MeOH): δ 6.50 (d, 1H), 7.05 (d, 1H), 7.25-7.60 (m, 6H), 7.70 (d, 1H), 7.95 (d, 2H), 8.15 (d, 1H)

Example 10

3-{4-Chloro-3-[(4-fluoro-biphenyl-3-carbonyl)-amino]-phenyl}-acrylic acid (52)

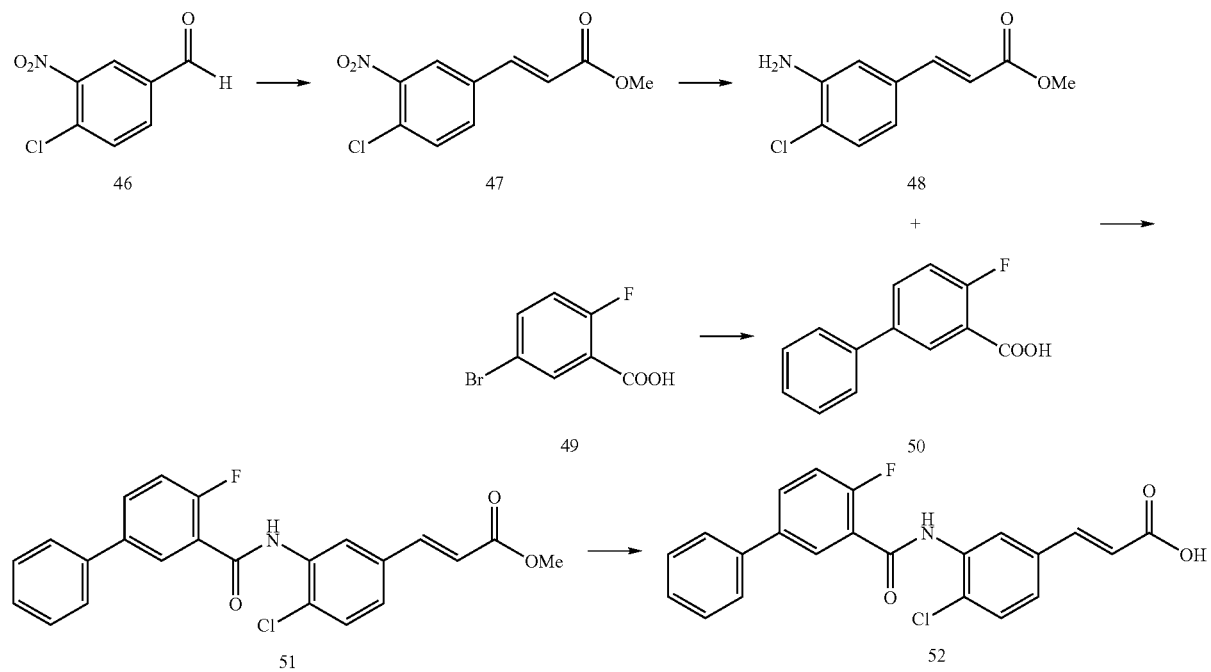

(a) 3-(4-Chloro-3-nitro-phenyl)-acrylic acid methyl ester (47)

Trimethyl phosphonoacetate (245 mg, 1.35 mmol) in THF (2.5 mL) was added dropwise (caution—vigorous reaction!) to sodium hydride (60% in oil) (83 mg, 2.02 mmol) under an atmosphere of nitrogen at 0° C. The reaction mixture was stirred for 15 minutes at 0° C. and then 4-chloro-3-nitrobenzaldehyde (46) (250 mg, 1.35 mmol) in THF was added dropwise. After 2 hours, water was added and the solvent concentrated in vacuo. The solid was filtered and dried to provide the crude title compound. Yield: 190 mg (b) 3-(3-Amino-4-chloro-phenyl)-acrylic acid methyl ester (48)

The crude nitro compound (47) (190 mg, 0.79 mmol) was reduced using Method A, except that SnCl$_2$.2H$_2$O (0.89 g, 3.94 mmol) and MeOH (2 mL) were used and the reaction was heated for 3 hours. The crude product was purified by column chromatography eluting with 10% EtOAc in heptane to give the title compound as a white solid. Yield: 69 mg (24% yield over two steps); LC-MS $t_r$ 1.32 min; MS (ES+) m/z 212 (M+H)

(c) 4-Fluoro-biphenyl-3-carboxylic acid (50)

5-Bromo-2-fluoro-benzoic acid (49) (2.0 g, 9.00 mmol) was coupled to phenyl boronic acid (1.23 g, 10.00 mmol) using method F, except that after the 2 hour reaction, water (50 mL) and TBME (50 mL) were added. The mixture was filtered and the aqueous layer was washed with TBME. The aqueous layer was then acidified with 1N HCl and the precipitated solid was collected and dried. Yield: 1.6 g, 82%

(d) 3-{4-Chloro-3-[(4-fluoro-biphenyl-3-carbonyl)-amino]-phenyl}-acrylic acid methyl ester (51)

To acid (50) (66 mg, 0.30 mmol) in DCM (1.3 mL) was added oxalyl chloride (39 mg, 0.30 mmol), a catalytic amount of DMF (1 drop) and the reaction stirred at ambient temperature for 1 hour. The solvent was concentrated in vacuo to provide the in situ acid chloride. To the acid chloride in DCM (1 mL) was added aniline (48) (64 mg, 0.30 mmol) in DCM (0.5 mL) then DIPEA (39 mg, 0.30 mmol) and the reaction mixture stirred at ambient temperature overnight. The solvent was concentrated in vacuo and the residue was purified using column chromatography eluting with 20% EtOAc in heptane to give the title compound. Yield: 124 mg, 100%; LC-MS $t_r$ 1.94 min; HPLC Purity: >69%; MS (ES+) m/z 410 (M+H)

(e) 3-{4-Chloro-3-[(4-fluoro-biphenyl-3-carbonyl)-amino]-phenyl}-acrylic acid (52)

The ester (51) (124 mg, 0.21 mmol) was hydrolysed using Method C, except that MeOH (1.25 mL), THF and 1M NaOH (1.25 mL) were used, and the reaction was stirred for 3 hours. The solvent was removed under a stream of nitrogen gas and the residue acidified with 1N HCl. The solid was filtered and dried to give the title compound. Yield: 91 mg, 76%; LC-MS $t_r$ 2.28 min; HPLC Purity: 94%; MS (ES+) m/z 396 (M+H); $^1$H NMR (400 MHz; DMSO): δ 6.60 (d, 1H), 7.45-7.75 (m, 7H), 7.80 (d, 2H), 7.95 (m, 1H), 8.10 (d, 1H), 8.15 (s, 1H), 10.25 (s, 1H), 12.55 (br. s, 1H)

Example 11

3-{3-[(4-Fluoro-biphenyl-3-carboximidoyl)-amino]-phenyl}-acrylic acid (58)

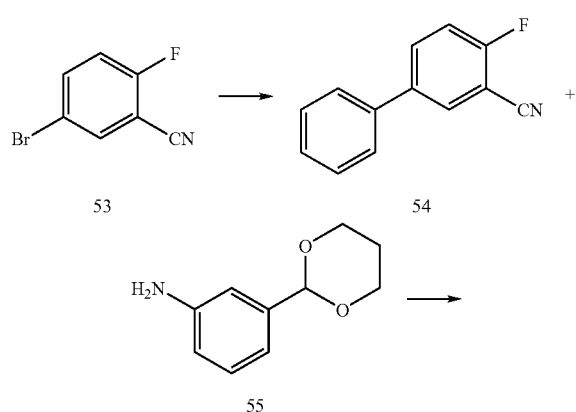

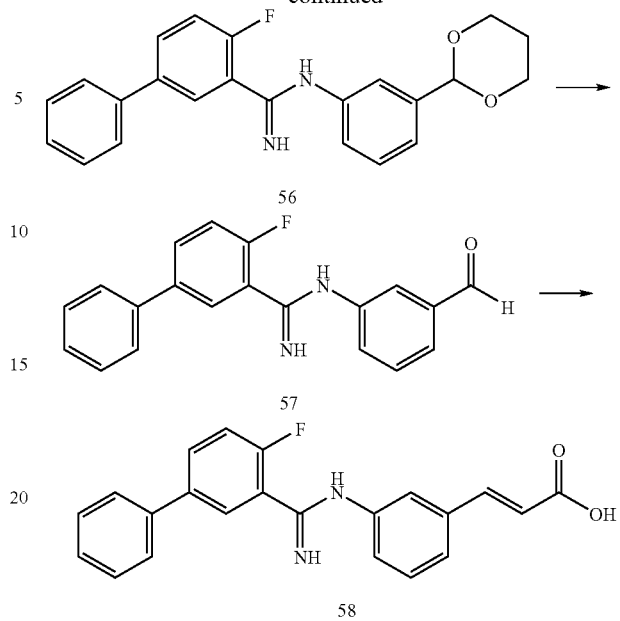

(a) 4-Fluoro-biphenyl-3-carbonitrile (54)

5-Bromo-2-fluorobenzonitrile (53) (500 mg, 2.54 mmol) was coupled to phenylboronic acid (335 mg, 2.75 mmol) with $Cs_2CO_3$ (1.63 g, 5.00 mmol) in toluene (4 mL) in a microwave at 140° C. for 30 minutes. Water was added and the organics extracted several times with EtOAc, dried (MgSO$_4$), filtered and the solvent concentrated in vacuo. The crude product was purified by Flash Master Jones Chromatography using a 25 g silica cartridge and eluting with 10% EtOAc in heptane to yield the title compound. Yield: 375 mg, 76%; LC-MS $t_r$ 1.63 min; HPLC Purity: 97%; MS (ES+) m/z not detectable (M+H)

(b) N-(3-[1,3]Dioxan-2-yl-phenyl)-4-fluoro-biphenyl-3-carboxamidine (56)

To 3-(1,3-dioxan-2-yl)aniline (55) (336 mg, 1.87 mmol) in toluene (7.5 mL) cooled to 0° C. was added a 2M trimethylaluminum solution in heptane (1.32 mL) dropwise and the resulting mixture was stirred at ambient temperature for 3.5 hours. The nitrile (54) (370 mg, 1.88 mmol) in toluene (7.5 mL) was added and the reaction heated to 70° C. overnight. The reaction was then cooled, poured onto a slurry of silica in DCM/MeOH and the organics flushed through with further DCM/MeOH. The filtrate was concentrated in vacuo and the residue purified by column chromatography using a gradient of EtOAc in heptane (5-100%) to yield the title compound. Yield: 378 mg, 53%; LC-MS $t_r$ 1.32 min; HPLC Purity: 71%; MS (ES+) m/z 377 (M+H)

(c) 4-Fluoro-N-(3-formyl-phenyl)-biphenyl-3-carboxamidine (57)

To acetal (56) (378 mg) in THF (2 mL) was added 1N hydrochloric acid (2 mL) and the reaction mixture stirred at ambient temperature overnight followed by heating to 50° C. for a further 3 hours. The reaction mixture was cooled to 0° C. and neutralised with saturated NaHCO$_3$ solution. The organics were extracted with EtOAc, dried (MgSO$_4$) and the solvent concentrated in vacuo to give the title compound. Yield: 307 mg, 96%; LC-MS $t_r$ 1.26 min; HPLC Purity: 71%; MS (ES+) m/z 319 (M+H)

(d) 3-{3-[(4-Fluoro-biphenyl-3-carboximidoyl)-amino]-phenyl}-acrylic acid (58)

Trimethyl phosphonoacetate (176 mg, 0.97 mmol) in THF (1.5 mL) was added dropwise (caution—vigorous reaction!) to sodium hydride (60% in oil) (58 mg, 1.46 mmol) under an atmosphere of nitrogen at 0° C. The reaction mixture was stirred for 15 minutes at 0° C. and then aldehyde (57) (307 mg, 0.97 mmol) in THF (1.50 mL) was added. After 3-hours further sodium hydride (60% in oil) (1.5 eq) was added and the reaction mixture stirred at ambient temperature overnight. Saturated NaHCO$_3$ solution was added and washed with EtOAc. The aqueous layer was acidified to pH 1 using 1.2 M HCl and extracted with EtOAc. The aqueous layer was then neutralised to pH 7 and extracted into EtOAc. The organic layers were combined, dried (MgSO$_4$) and the solvent concentrated in vacuo. The residue was purified by Flash Master Jones Chromatography using a 2 g silica cartridge and a gradient of EtOAc in heptane and MeOH in EtOAc to yield the title compound. Yield: 25 mg, 7%; LC-MS $t_r$ 1.77 min; HPLC Purity: 91%; MS (ES+) m/z 361 (M+H); NMR (400 MHz; MeOH): δ 6.6 (d, 7.35-7.80 (m, 11H), 8.05 (m, 1H), 8.15 (d, 1H)

Example 12

Biological Results

Binding Ability to Human EP Receptors

Membranes were prepared from cells stably transfected with human EP receptor cDNA. In brief, cells were cultured to confluency, scraped from culture flasks, and centrifuged (800 g, 8 minutes, 4° C.). Cells were twice washed in ice cold homogenisation buffer containing 10 mM Tris-HCl, 1 mM EDTA.2Na, 250 mM sucrose, 1 mM PMSF, 0.3 mM indomethacin, pH 7.4, homogenised and re-centrifuged as before. The supernatant was stored on ice and pellets re-homogenised and re-spun. Supernatants were pooled and centrifuged at 40000 g, 10 minutes, 4° C. Resultant membrane pellets were stored at −80° C. until use.

For assay, membranes expressing human EP$_4$, EP$_3$, EP$_2$ or EP$_1$ receptors were incubated in Millipore (MHVBN45) plates containing assay buffer, radiolabelled [$^3$H]PGE$_2$ and 0.1 to 10 000 nM concentrations of compounds. Incubations were performed at suitable temperatures and for suitable times to allow equilibrium to be reached. Non-specific binding was determined in the presence of 10 uM PGE$_2$. Bound and free radiolabel was separated by vacuum manifold filtration using appropriate wash buffers, and bound radiolabel was determined by scintillation counting. Constituents of each of the buffers are included in table 1 below.

The affinity or pK$_i$ of each compound for each receptor was calculated from the concentration causing 50% radioligand displacement (IC$_{50}$) using the Cheng-Prusoff equation:

$$Ki = \frac{IC_{50}}{1 + \left(\frac{\text{radioligand concentration}}{\text{radioligand } KD}\right)}$$

This approach follows that set out in Kenakin, T. P., Pharmacologic analysis of drug receptor interaction. Raven Press, New York, 2$^{nd}$ edition.

TABLE 1

| Receptor | | EP$_1$ | EP$_2$ | EP$_3$ | EP$_4$ |
|---|---|---|---|---|---|
| Protein/well | | 6.5 μg | 8 μg | 5 μg | 5 μg |
| Final [$^3$H-PGE$_2$] | | 3.6 nM | 3 nM | 2.5 nM | 1 nM |
| Buffer | Assay | 10 mM MES pH 6.0; 10 mM MgCl$_2$; 1 mM EDTA, 3 uM Indomethacin | 10 mM MES pH 6.0; 10 mM MgCl$_2$; 1 mM EDTA | 10 mM MES pH 6.0; 10 mM MgCl2; 1 mM EDTA, 100 uM GTP-gamma-S | 10 mM MES pH 6.0; 10 mM MgCl$_2$; 1 mM EDTA, 3 uM Indomethacin |
| | Wash | 10 mM MES pH 6.0; 10 mM MgCl$_2$ | 10 mM MES pH 6.0; 10 mM MgCl$_2$ | 10 mM MES pH 6.0; 10 mM MgCl$_2$ | 10 mM MES pH 6.0; 1 mM EDTA |

Determination of Agonist Activity at Recombinant Human EP$_2$ Prostanoid Receptors and Antagonist Activity at EP$_4$ Prostanoid Receptors HEK-293 cell clones stably transfected with human EP$_2$ or EP$_4$ prostanoid receptors were cultured at 37° C. in a 5% CO$_2$ incubator, in 96-well poly-L-lysine coated plates at a density of 50,000 cells/well. Culture media was Minimal essential media (MEM), supplemented with 10% foetal bovine serum, 100 U/ml penicillin, 100 ng/ml streptomycin, 2.5 μg/ml fungizone, 2 mM glutamine. Cells were cultured to confluency (3-4 days) prior to use.

Culture media was removed, and confluent cells washed three times in MEM. 175 μl assay buffer (MEM containing no supplements+1 mM IBMX) was incubated with the cells for 60 min. Cells were then stimulated by the addition of 25 μl of PGE$_2$ or agonists prepared in assay buffer. In antagonist studies, cells were pre-incubated with compounds for 30 minutes prior to PGE$_2$-mediated stimulation Plates were incubated for 15 min at 37° C., before termination of the reaction by the addition of 25 μl 1M HCl. The plate was then frozen at −20° C. overnight before determination of cAMP concentration.

Stimulated cAMP levels were determined by radioligand displacement binding. In brief, plates were thawed rapidly in a waterbath, and the samples neutralised by the addition of 25 μl 1M NaOH. 30 μl was transferred to Millipore plates pre-coated with 0.5% Polyethylenimine (PEI). Samples were diluted by addition of 90 μl cAMP determination buffer (50 mM Tris, 5 mM EDTA, pH 7.0). A cAMP standard curve (10$^{-11}$M to 10$^{-5}$M) was constructed. 15 μl of 2 nM (final concentration) [$^3$H] cAMP, and 15 μl of 3'5'-cAMP protein kinase (8 μg/well final concentration) prepared in cAMP determination buffer containing 0.1% BSA, were added to each well.

Plates were incubated on ice for 2 hours, before bound and free radiolabel were separated by vacuum filtration harvesting using the Millipore vacuum manifold, using ice cold water as the termination buffer.

The sealing mat was removed from the Millipore plates, and the filters allowed to dry overnight. 50 μl Microscint 0 (Packard Bioscience) was added to each well, and the plate counted using the Micro-Beta Trilux topcount ³H program.

cAMP accumulation was determined from the standard curve, and values calculated in pmoles cAMP/well. Antagonists affinities ($pA_2$ values) were determined assuming a slope of unity and the Gaddam-Schild equation, where $pA_2$=log[concentration ratio-1]−log[antagonist]. Agonist potencies were determined from log $EC_{50}$ values, denoting the concentration of agonist required to produce 50% of the agonist response.

TABLE 2

| Compound | pKi (M) | |
| --- | --- | --- |
|  | $EP_2$ | $EP_4$ |
| 5 | >7 | <6 |
| 11 | >7 | <6 |
| 16 | >6 | <6 |
| 20 | >7 | <6 |
| 28 | >6 | <6 |
| 29 | >6 | <6 |
| 34 | >6 | <6 |
| 40 | >6 | <6 |
| 45 | >7 | <6 |
| 52 | >8 | <7 |
| 58 | >6 | <6 |

The invention claimed is:

1. A compound of formula (III):

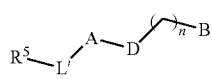
(III)

or a salt or an ester thereof, wherein:
R⁵ is phenyl or substituted phenyl wherein each substitution is independently selected from the group consisting of $C_{1-4}$ alkoxy, $C_{1-4}$ alkyl, halo, acyl, and amino;
L' is a single bond, —O— or —C(=O)—;
A is selected from the group consisting of:

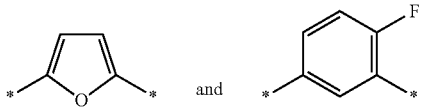

D is selected from:

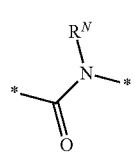
(i)

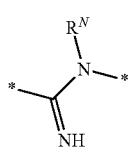
(ii)

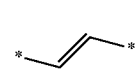
(iii)

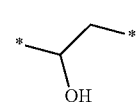
(iv)

B is selected from the group consisting of:

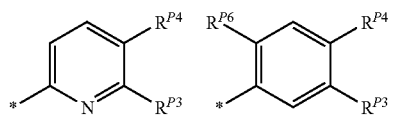

where $R^{P6}$ is selected from fluoro and chloro;
where $R^{P4}$ is H and $R^{P3}$ is —CH=CH—R²;
n is 0 or 1;
$R^N$ is H or optionally substituted $C_{1-4}$ alkyl; and
R² is either:
(i) —CO₂H;
(ii) —CONH₂;
(iii) —CH₂—OH; or
(iv) tetrazol-5-yl.

2. A compound according to claim 1, wherein R⁵ is phenyl.

3. A compound according to claim 1, wherein L' is a single bond.

4. A compound according to claim 1, wherein D is

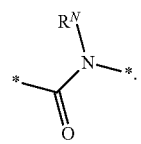

5. A compound according to claim 4, wherein $R^N$ is H.

6. A compound according to claim 1, wherein B is:

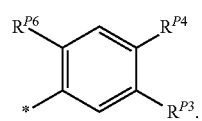

7. A compound according to claim 1, wherein R² is —CO₂H.

8. A compound according to claim 1, wherein n is 0.

9. A pharmaceutical composition comprising a compound according to claim 1, or a pharmaceutically acceptable salt thereof, together with a pharmaceutically acceptable carrier or diluent.

10. The compound according to claim 6 wherein L' is a single bond.

11. The compound according to claim 10 where D is

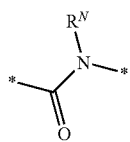

and $R^N$ is H.

12. The compound according to claim 11 wherein n is 0.

13. The compound according to claim 11 wherein $R^2$ is —$CO_2H$.

14. The compound according to claim 13 wherein $R^5$ is phenyl or substitued phenyl wherein each substitution is independently selected from the group consisting of $C_{1-4}$ alkoxy, $C_{1-4}$ alky, halo, acyl, and amino.

15. The compound according to claim 13 wherein $R^5$ is phenyl or substituted phenyl wherein each substitution is independently selected from the group consisting of —$OCH_3$, —$OCF_3$, —$OCH_2CH_3$, —$OCHF_2$, —$CH_3$, —$CF_3$, —$CH(CH_3)_2$, Cl, and F.

16. The compound according to claim 15 wherein n is 0.

17. The compound according to claim 16 wherein $R^5$ is phenyl.

18. The compound according to claim 1 wherein $R^5$ is phenyl or substituted phenyl wherein each substitution is independently selected from the group consisting of —$OCH_3$, —$OCF_3$, —$OCH_2CH_3$, —$OCHF_2$, —$CH_3$, —$CF_3$, —$CH(CH_3)_2$, Cl, and F.

19. The compound according to claim 18 wherein $R^2$ is —$CO_2H$.

20. The compound according to claim 19 wherein n is 0.

21. The compound according to claim 20 wherein $R^5$ is phenyl.

* * * * *